United States Patent
Riley

(10) Patent No.: US 10,548,779 B2
(45) Date of Patent: Feb. 4, 2020

(54) FACIAL STRUCTURE STABILIZATION METHODS AND APPARATUS

(71) Applicant: Mary Frances Riley, Houston, TX (US)

(72) Inventor: Mary Frances Riley, Houston, TX (US)

( * ) Notice: Subject to any disclaimer, the term of this patent is extended or adjusted under 35 U.S.C. 154(b) by 343 days.

(21) Appl. No.: 15/372,670

(22) Filed: Dec. 8, 2016

(65) Prior Publication Data

US 2017/0143555 A1    May 25, 2017

Related U.S. Application Data

(63) Continuation of application No. 14/344,860, filed as application No. PCT/US2012/058540 on Oct. 3, 2012, now Pat. No. 9,526,661.

(60) Provisional application No. 61/545,121, filed on Oct. 8, 2011.

(51) Int. Cl.
 *A61F 13/12* (2006.01)
 *A61F 9/04* (2006.01)

(52) U.S. Cl.
 CPC .............. *A61F 13/122* (2013.01); *A61F 9/04* (2013.01); *A61F 9/045* (2013.01)

(58) Field of Classification Search
 CPC .......... A61F 13/122; A61F 9/04; A61F 9/045; A61F 7/10; A61F 13/124; A61F 13/12; A61F 5/08
 See application file for complete search history.

(56) References Cited

U.S. PATENT DOCUMENTS

| | | |
|---|---|---|
| 765,361 A | 7/1904 | Hargrave |
| 4,190,054 A | 2/1980 | Brennan |
| 4,995,379 A | 2/1991 | Brooks |
| 5,031,609 A | 7/1991 | Fye |
| 5,116,675 A | 5/1992 | Nash-Morgan |
| 5,370,117 A | 12/1994 | McLaurin |
| 5,555,900 A | 9/1996 | Rich |
| 5,582,585 A | 12/1996 | Nash-Morgan |
| 5,693,164 A | 12/1997 | Chang |
| 5,961,479 A | 10/1999 | Reeves et al. |
| 6,039,710 A | 3/2000 | Kelley et al. |
| 6,512,159 B1 | 1/2003 | Shesol |
| 6,758,720 B2 | 7/2004 | Chen |
| 6,780,081 B2 | 8/2004 | Chen et al. |
| 6,857,932 B2 | 2/2005 | Chen |
| 7,219,669 B1 | 5/2007 | Lowell, Jr. et al. |
| 7,278,899 B2 | 10/2007 | Davis |

(Continued)

FOREIGN PATENT DOCUMENTS

JP    2003111782 A    4/2003

OTHER PUBLICATIONS

International search report, PCT/US2012/058540, dated Dec. 6, 2012.

(Continued)

*Primary Examiner* — Ophelia A Hawthorne
(74) *Attorney, Agent, or Firm* — Blank Rome LLP

(57) ABSTRACT

Apparatus are described for providing support and maintenance of facial structures using facial support members that include internal silicone gel pads that are encased in an elastomeric casing and are dimensioned to apply downward pressure to tissues underlying the facial support members.

23 Claims, 20 Drawing Sheets

(56) References Cited

U.S. PATENT DOCUMENTS

| | | |
|---|---|---|
| 7,290,548 B2 | 11/2007 | Ungemach |
| 7,559,907 B2 | 7/2009 | Krempel et al. |
| 8,254,621 B2 | 8/2012 | Silvestri et al. |
| 8,257,385 B2 | 9/2012 | Karnwie-Tuah |
| 2004/0138699 A1 | 7/2004 | Lish |
| 2005/0187502 A1 | 8/2005 | Krempel |
| 2006/0106330 A1 | 5/2006 | Andrade et al. |
| 2008/0161892 A1 | 7/2008 | Mercuro |
| 2011/0081333 A1* | 4/2011 | Shantha ................. A61N 1/328 424/94.62 |

OTHER PUBLICATIONS

Face Lift Compression Garments, Bella-Jane, http://www.bella-jane.comlhead_and_facial_20_ctg.htm, Feb. 28, 2011, 11 pages.

Face Lift Compression Garments, http://www.makemeheal.com, Feb. 28, 2011, 18 pages.

"European Application Serial No. 12838772.7, European Search Report dated Oct. 19, 2015" 13 pages.

* cited by examiner

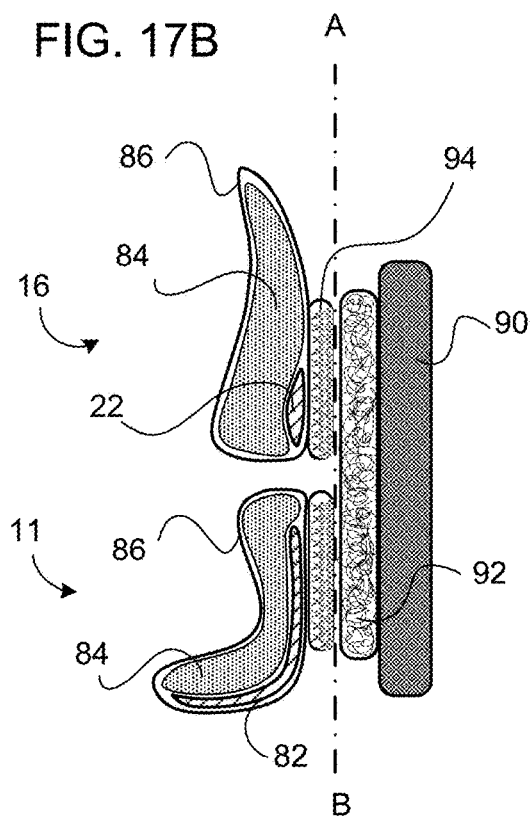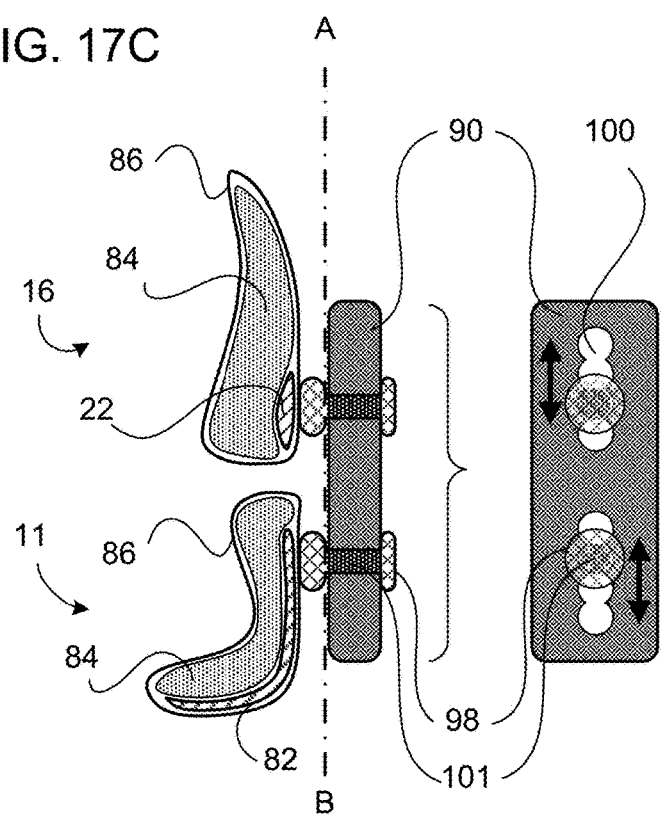

FACIAL STRUCTURE STABILIZATION METHODS AND APPARATUS

CROSS REFERENCE TO RELATED APPLICATIONS

This application claims priority based on U.S. application Ser. No. 14/344,860 filed Mar. 13, 2014 and issuing as U.S. Pat. No. 9,526,661 on Dec. 27, 2016, which claims priority to PCT/US2012/058540, filed on Oct. 3, 2012 and published as WO2013/052534, which in turn claims priority to U.S. Provisional Application Ser. No. 61/545,121 filed on Oct. 8, 2011, which applications are incorporated herein by reference.

FIELD OF THE INVENTION

This disclosure relates generally to devices and methods for positional maintenance of facial structures and facial implants.

BACKGROUND OF THE INVENTION

Without limiting the scope of the invention, its background is described in connection with existing devices for healing after plastic surgical interventions. Patients who undergo plastic surgery procedures such as cheek implant surgery or chin implant surgery are customarily provided compression "masks" or bandages for a few days or weeks following the surgery to maintain the implants in proper position during the healing process, particularly during the time when post-surgical swelling around the implant site is subsiding and the implant positions are becoming established in their desired locations. These support devices typically are in the form of elastic bandages that may be specifically designed to hold underlying surgical bandages and/or cooling gel or "ice" packs in place. Also available are partial and full facial plastic surgery compression garments such as those depicted in Shesol et al. U.S. Pat. No. 6,512,159, Kelly et al. U.S. Pat. No. 6,039,710 and Reeves U.S. Pat. No. 5,961,479. While these devices may be recommended immediately following surgery, they are cumbersome and generally uncomfortable and are not designed or desirable for prolonged use. Furthermore, existing devices are not susceptible to custom fitting.

In addition to unmet needs for comfortable unobtrusive positional maintenance devices, solutions for maintenance of facial structures with aging are not available. With aging, the muscles of the face become thinner and longer. Fat deposits that veneer the musculature during youth are lost with aging resulting in progressively hollow facial structures covered with sagging skin. Non-surgical solutions for tightening the skin have been proposed including the elasticized adhesive facial gathering strips disclosed by Nash-Morgan in U.S. Pat. No. 5,116,675. A facial toning device including adhesive pads was disclosed by Karnwie-Tuah in U.S. Pat. No. 8,257,385. The Karnwie-Tuah device is described as a pair of adhesive pads for adhering to the user's facial skin, a pair of supporting earpieces connected to the adhesive pads, and a strap behind the head connecting the pair of earpieces. The length of the back strap is adjusted until a desired tension is placed on the pads, which causes the pads to stretch the skin and allegedly tone the facial and upper neck muscles naturally over a period of time. However, such devices do not apply direct pressure to the underlying structures.

Dry eye is a further condition that is associated with aging as well as certain diseases such as Grave's Opthalmopathy and Sjogren's Syndrome. Existing devices for keeping the eyes closed and humidified during rest are available as modified goggles. However, these devices require a strap going around the head and are frequently dislodged during sleep.

From the foregoing it is apparent the there is a need in the art for positional maintenance of facial structures and facial fillers such as implants and injectables. Disclosed herein are devices and methods to accomplish such ends. Also disclosed are devices for positional control of the eyelids during rest.

BRIEF SUMMARY OF THE INVENTION

Certain embodiments disclosed herein are directed to methods and apparatus for extended support and maintenance of facial structures by molding and maintaining the skin and underlying fat, fillers and muscle with supportive soft silicone gel pads that apply desired pressure to the structures underlying the skin.

In one embodiment, a facial support apparatus is provided that includes a pair of ear connection members connected to at least one pair of facial region support members, wherein each facial region support member comprises an inner skin facing surface that is releasably self-adhesive to a user's skin. In certain embodiments the facial region support members are largely formed of medical grade silicone. For example, in certain embodiments each of the pair of cheek supports comprises an inner skin facing adhesive layer and an outer non-adhesive layer wherein the inner and outer layers enclose a silicone gel filling. Certain embodiments provide for custom fitting to the user by including portions of thermoplastic or moldable metal support armature structures enabling form fitting to a user's facial anatomy by heating and cooling or bending.

In certain embodiments, the facial support apparatus includes a pair cheek supports and each cheek support extends from one of the pair of ear connection members across at least a portion of a cheek bone of a user. The apparatus supports the skin as well as the musculature of the check while sleeping, resting, exercise or normal daily activities.

In another embodiment, the skin as well as the musculature of the lower jaw is supported while sleeping, resting or exercising where the at least one facial region support member is a chin support attaching to and extending between each of the ear connection members.

In another embodiment, the skin as well as the musculature of the forehead is supported where the at least one facial region support member is a forehead support attaching to and extending between each of the ear connection members. In certain embodiments, the forehead support is adjustable thus allowing upward tension to be place on other attached facial regions supports such as cheek and/or mandible supports. In further embodiments, the forehead support is in connection with a back neck strap that may be elastomeric and/or may be further adjustable both to customize the fit to the wearer and to provide stability and tension. In certain embodiments a plurality of facial region support members is provided including at least two different facial region support members selected from the group consisting of: a pair of cheek supports, a chin support and a forehead support.

In one embodiment a facial support apparatus is provided that includes a facial region support member connected to an ear connection member, wherein the facial region support member comprises a silicone gel pad encased in an elastomeric casing and wherein the silicone gel pad is adapted and dimensioned to apply downward pressure to a facial structure underlying placement of the silicone gel pad. The facial region support member further includes a support armature in certain embodiments. The support armature may be supplied with a fixed shape or may be a moldable structure enabling form-fitting to a user's facial anatomy. In certain embodiments the ear connection member includes an ear bud that confers stability to the ear connection. In certain embodiments the facial region support members are attached to the ear connection member by a moveable attachment that allows for adjusting of the placement of the facial region supports to fit different individuals. One example of a moveable attachment is a hook and loop fastening mechanism, such as a VELCRO brand hook and loop fastening mechanism.

Also provided are eyelid closure devices. In one embodiment the device includes a pair of eyelid covers connected to a nose bridge that includes a moldable structure such as a thermoplastic structure or a shape retaining metal that is custom fittable to a user. In certain embodiments the eyelid covers include silicone gel pads that comfortably conform to the shape of the underlying eyeball. The eyelid covers may be further connected to a pair of ear straps. Alternatively the eyelid covers may be held in place with a hypoallergenic releasable and reusable adhesive.

BRIEF DESCRIPTION OF THE DRAWINGS

For a more complete understanding of the present invention, including features and advantages, reference is now made to the detailed description along with the accompanying figures:

FIG. 17B depicts a side view cross-section through the indicated portion of FIG. 17A wherein the adjustment mechanism includes hook and loop attachments. FIG. 17C depicts a side view cross-section through the indicated portion of FIG. 17A wherein the adjustment mechanism includes a locking slot and a catch-up pin.

DETAILED DESCRIPTION OF THE INVENTION

Figure 1:
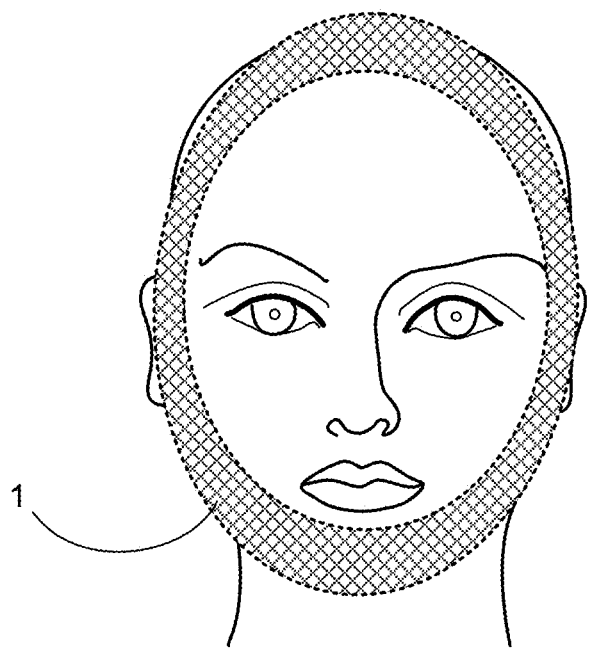
FIG. 1 illustrates a prior art post-surgical chin strap.
Figure 2:
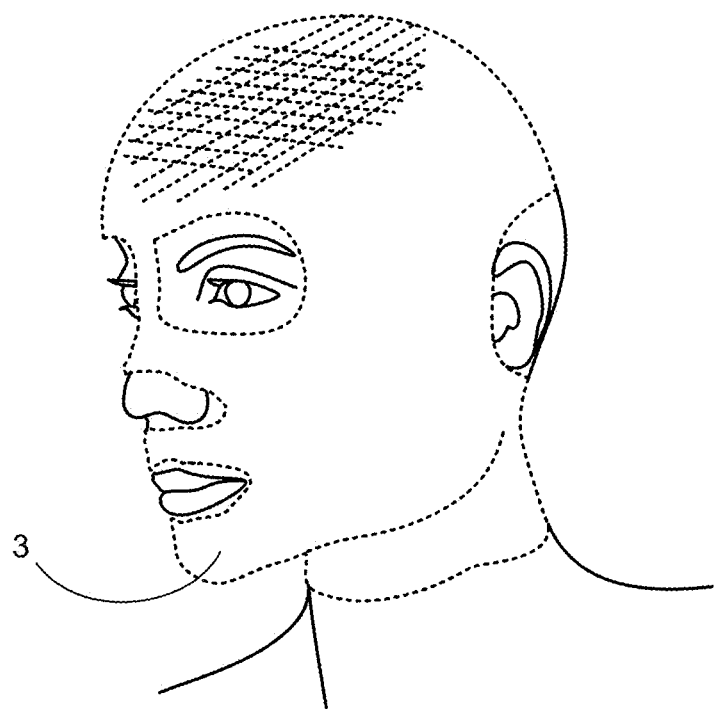
FIG. 2 illustrates a prior art post-surgical full face mask.

While the making and using of various embodiments of the present invention are discussed in detail below, it should be appreciated that the present invention provides many applicable inventive concepts which can be employed in a wide variety of specific contexts. The specific embodiment discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

In one embodiment of the present invention positional maintenance support devices are provided that are suitable for prolonged wear and designed to greatly extend the customary life of facial implants by maintaining them in the desired position and shape. Such use may, for example, be nightly, to provide gentle support as well as protection against contact deformation of the implants. As such, the facial support devices must by comfortable to wear over substantial periods of time, in terms of feel, pressure, and freedom from allergic reactions or other irritation. Silicone rubber is a presently available compound that provides the desirable properties of being hypoallergenic, non-reactive, elastic, color matchable, lightweight, and able to adhere to the skin without the use of adhesives. Medical grade silicone rubber (polysiloxane) is sufficiently biocompatible to be implantable and is considered desirable for the present indications.

The use of medical grade silicone rubber for construction of the positional maintenance devices disclosed herein enables production of devices having the necessary combinations of shape and elasticity required for individual implant patients, and which can be worn comfortably by those patients for the extended times envisioned. In this way the life of the implants may be greatly extended and the need for additional surgery to maintain the desired appearance may be greatly reduced, thus improving the patients' experience while reducing the expense incurred. Silicone rubber sheeting is believed to improve healing of damage to the skin and is currently used in wound healing, burn healing and reduction of scar formation. The custom fittable facial supports disclosed herein are well suited and applicable for such indications.

The positional supports provided herein may be manufactured in a set of sizes that will be useful for most individuals. Alternatively, any of the positional support or control devices disclosed herein can be custom fit. In embodiments including silicone gel pads, the silicone gel that is employed may be a soft, essentially sticky material that must have a protective skin. Such skins can be inner and outer sheets that form an enclosing casing in which the silicone gel is formed into a desired shape during manufacturing. The enclosing casing enables molding and preserves the integrity of the friable soft silicone. Such silicone gel pads, when formed, are injected or pored as liquid silicone into an enclosing casing disposed in a mold having the desired shape that would comfortably fit over the body structure that is being covered, in this case a cheek, mandible, or eyeball, and then heat cured into the shape. A particularly suitable silicone gel is disclosed in U.S. Pat. No. 5,693,164 wherein the silicone gel material inside of the outer sheets results from curing various compositions and amounts of silicone oils, resins, inhibitors, catalysts and pigments. As disclosed in U.S. Pat. No. 5,693,164, the inner and other sheets that form the casing may be polyurethane films having a thickness between 20 to 70 micrometers. In one embodiment, the silicone gel pad is integral to the device body while in alternative embodiment the silicone gel pad is inserted into a pocket that is formed in the device body.

Suitable thermoplastic materials formulated for ease of low temperature molding with minimal shrinkage and sufficient post molding rigidity are presently available for use in forming the semi-rigid support armatures of certain embodiments disclosed herein. For example thermoplastic sheets composed of a blend of polycaprolactone polyester resin and inert fillers are available from Klarity Medical Products, Newark, Ohio.

Figure 3A:
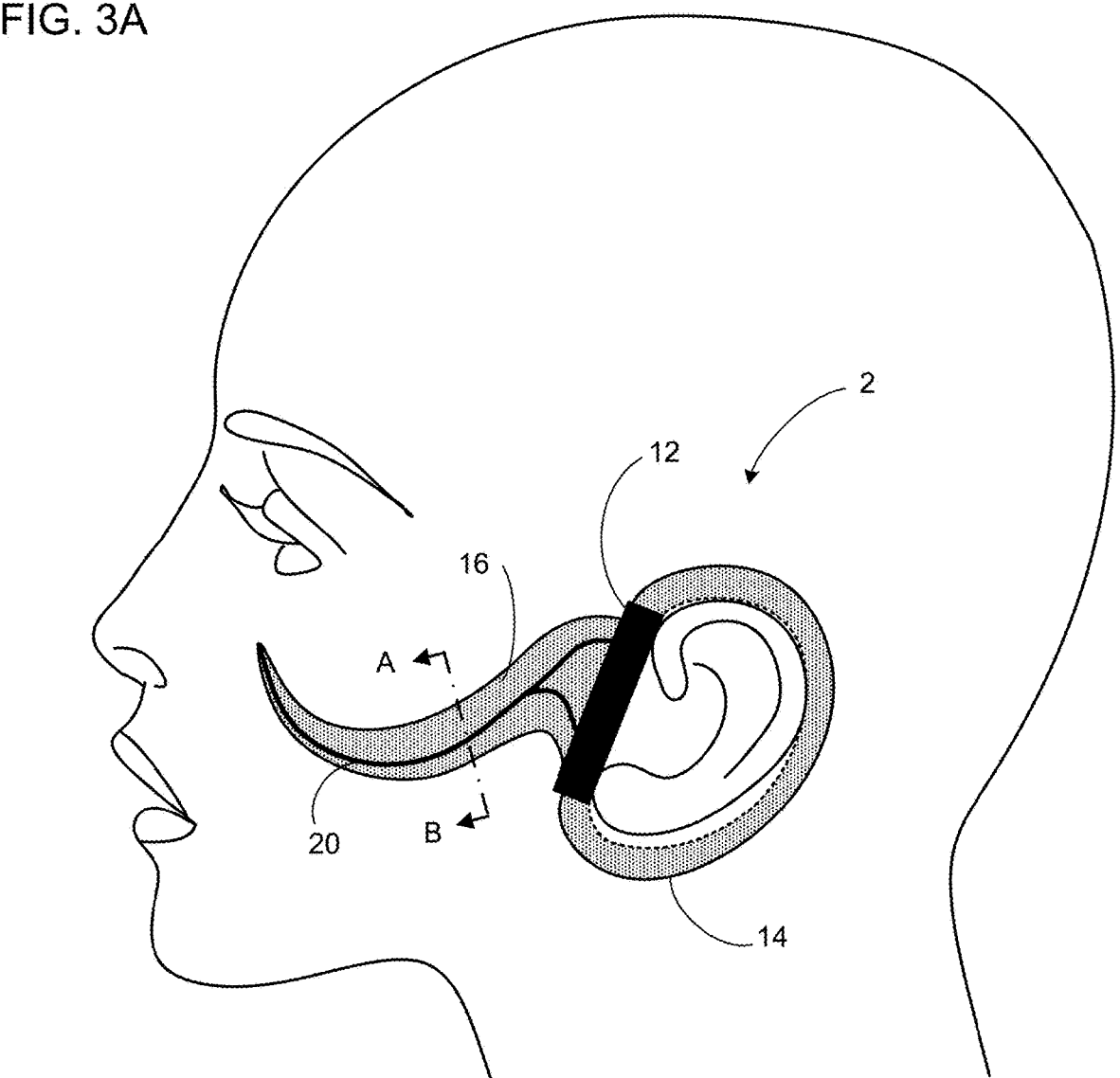
FIG. 3A illustrates a side view of a cheek positional support according to an embodiment of the invention.
Figure 3B:
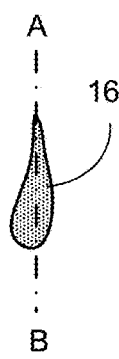
FIG. 3B depicts a cross section A-B according to one embodiment.
Figure 3C:
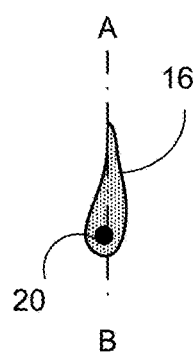
FIG. 3C depicts a cross section A-B according to another embodiment.
Figure 3D:
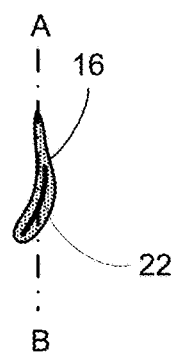
FIG. 3D depicts a cross section A-B according to another embodiment.

With respect to a cheek or cheek implant support, as depicted in FIG. 3A, support device 2 may be in the form of an apparatus that has individual cheek supports 16 resting on a lower aspect of, or below, the cheek bones. Cheek supports 16 extend from bar 12. Bar 12 is in turn held in place by ear strap 14. Ear strap 14 may be composed of an elastic material such as silicone sheeting if desired. As depicted in the cross-sections of various embodiments of individual cheek support arm 16, the arms may optionally include a semi-rigid support armature 20 that may be internal or externally affixed to cheek support 16. Support armature 20 as depicted is a preformed structure or is a formable metal wire or thermosetting plastic that is deformable to custom fit the face of the wearer. FIG. 3C depicts a wire in cross section while FIG. 3D depicts a strip or sheet material. The support armature 20 may, optionally and as depicted, be buttressed in its attachment to bar 12. Alternatively, the armature may be a strip 22 of either metal or thermosetting plastic as shown in FIG. 3D. The cheek supports include or are formed of a silicone gel pad encased in an elastomeric casing. The three dimensional shape of the silicone gel pads provides for applied pressure to the underlying structures such as fat, muscle and/or implants and provides support for and shaping of these structures.

Figure 4A:
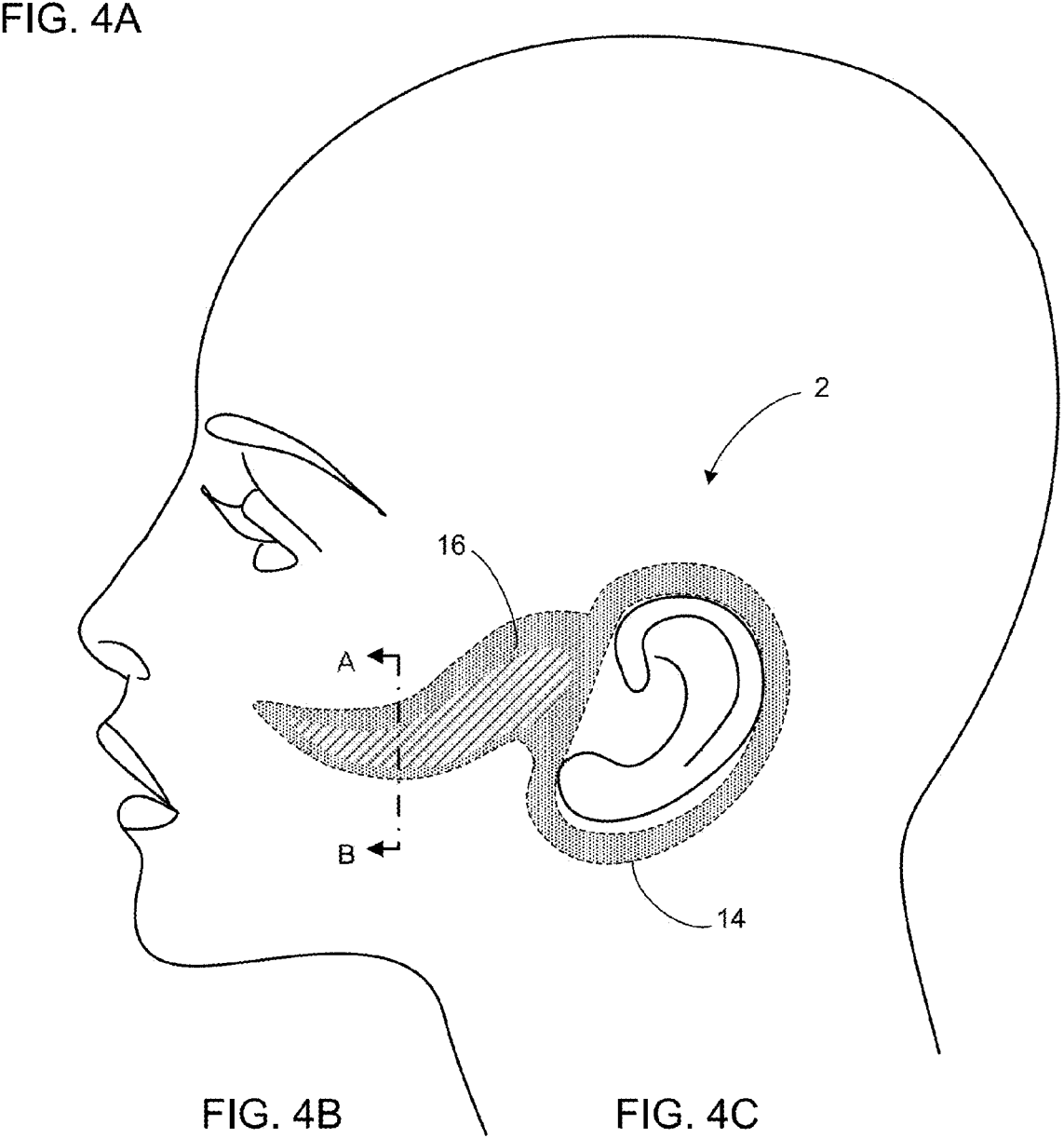
FIG. 4A illustrates a side view of a cheek positional support according to an embodiment of the invention.
Figure 4B:
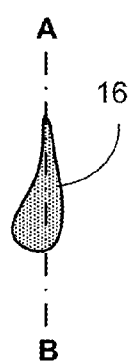
FIG. 4B depicts a cross section through a central portion of the cheek support of FIG. 4A according to one embodiment.

FIG. 4A depicts one embodiment in which a cheek support is provided in the form of an integral ear piece 14 and cheek support 16 that is self-adhesive. The support 2 is applied before bedtime or rest and acts to support facial structures during rest. Alternatively, the support may be applied prior to exercise or any activity where positional support may be desired. The gentle tension and pressure provided by the device acts to retain a desirable position of underlying facial structures and counteract the effect of gravity that gradually result in sagging and the appearance of aging. Where facial implants exist, the cheek support controls the movement of the implants in the originally desired position by application of gentle pressure. The tear drop shaped cross section of FIG. 4B is described in more detail in reference to FIG. 12. In the case of the tear drop shaped positional support of FIG. 4B, an internal silicone gel pad provides the shape of the support. One desirable location of increased thickness of the support is shown by cross-hatching in FIG. 4A.

Figure 4C:
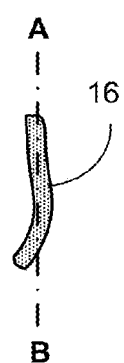
FIG. 4C depicts a cross section through a central portion of the cheek support of FIG. 4A according to another embodiment.

In alternative embodiments, and as depicted in FIG. 4C, the support may be in the form of silicone sheeting such as described in reference to certain surgical bandages. The silicone sheeting is formed such that the outer surface is non-adhesive while the inner skin facing layer is releasably and reusably self-adhesive. The support is preferably formed of clear or skin toned material that is imperceptible at a distance.

Figure 4D:
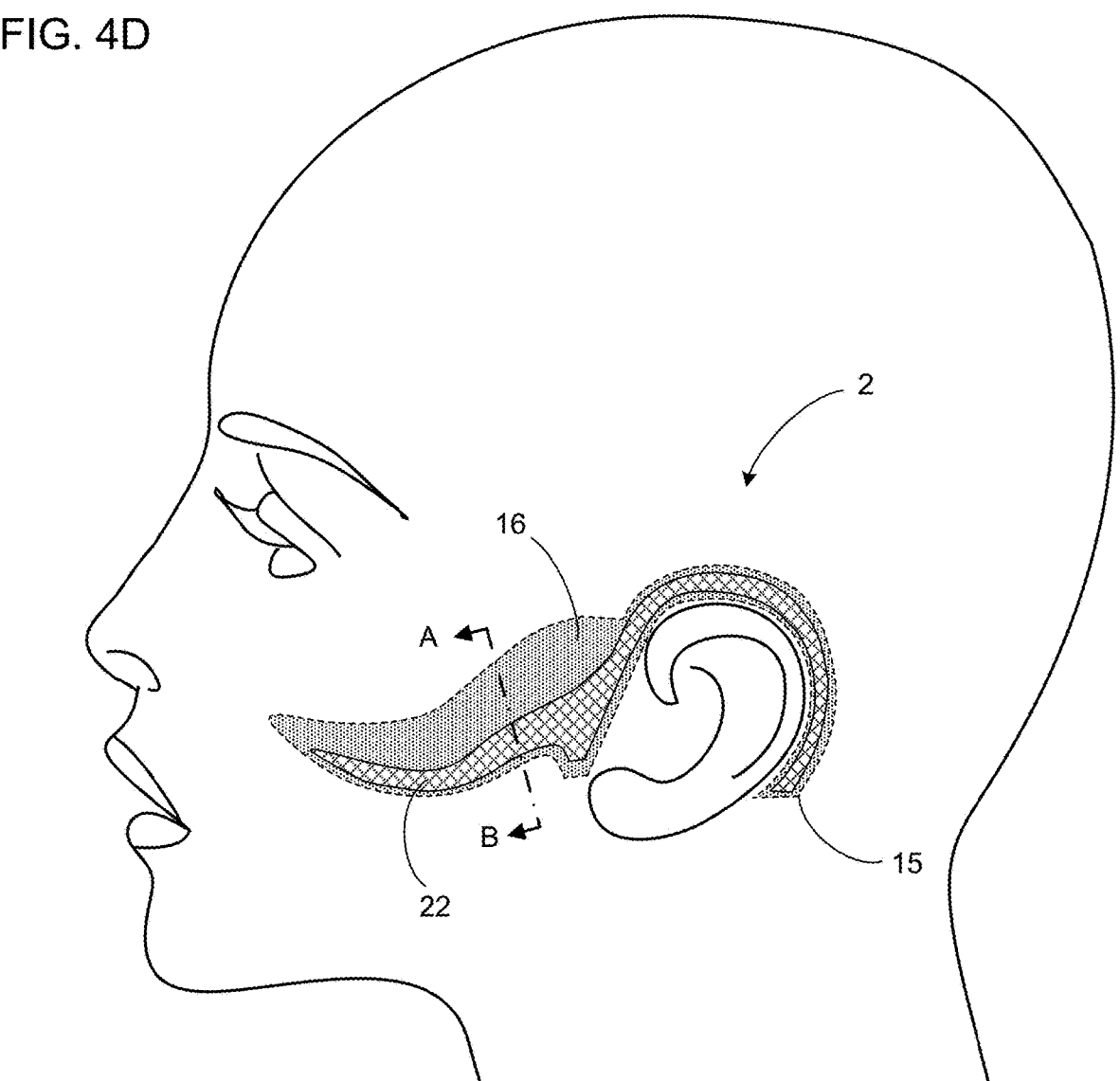
FIG. 4D illustrates a side view of a cheek positional support according to an alternative embodiment of the invention including a rigid internal member.
Figure 4E:
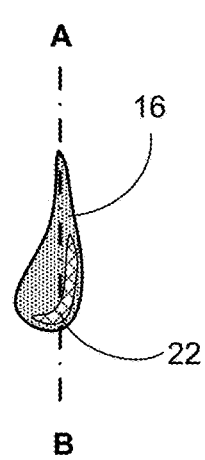
FIG. 4E depicts a cross section through a central portion of the cheek support of FIG. 4D.
Figure 17A:
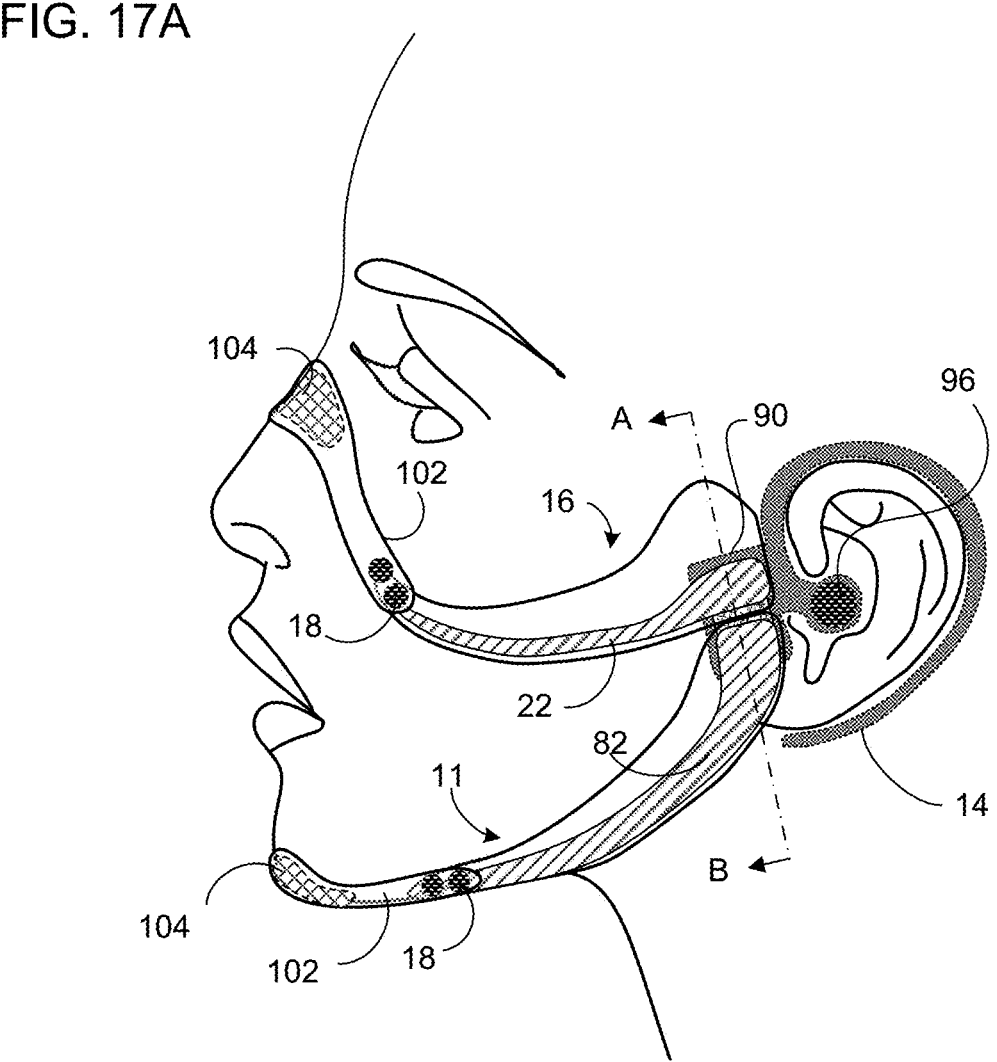
FIG. 17A depicts another embodiment of a chin and cheek support including an ear piece secured by an ear bud.

In the embodiment depicted in FIG. 4D and FIG. 4E, cheek support 16 includes semi-rigid support member 22 that may have a prefixed shape or may be deformable to custom fit to the individual wearer. The semi-rigid support member 22 may be internal or external to the cheek or chin supports. In the depicted embodiment, semi-rigid support member 22 extends into ear piece 15 that loops over the ear but does not encircle the ear. The ear piece may include a stabilizing ear bud as depicted in FIG. 17A.

Figure 5A:
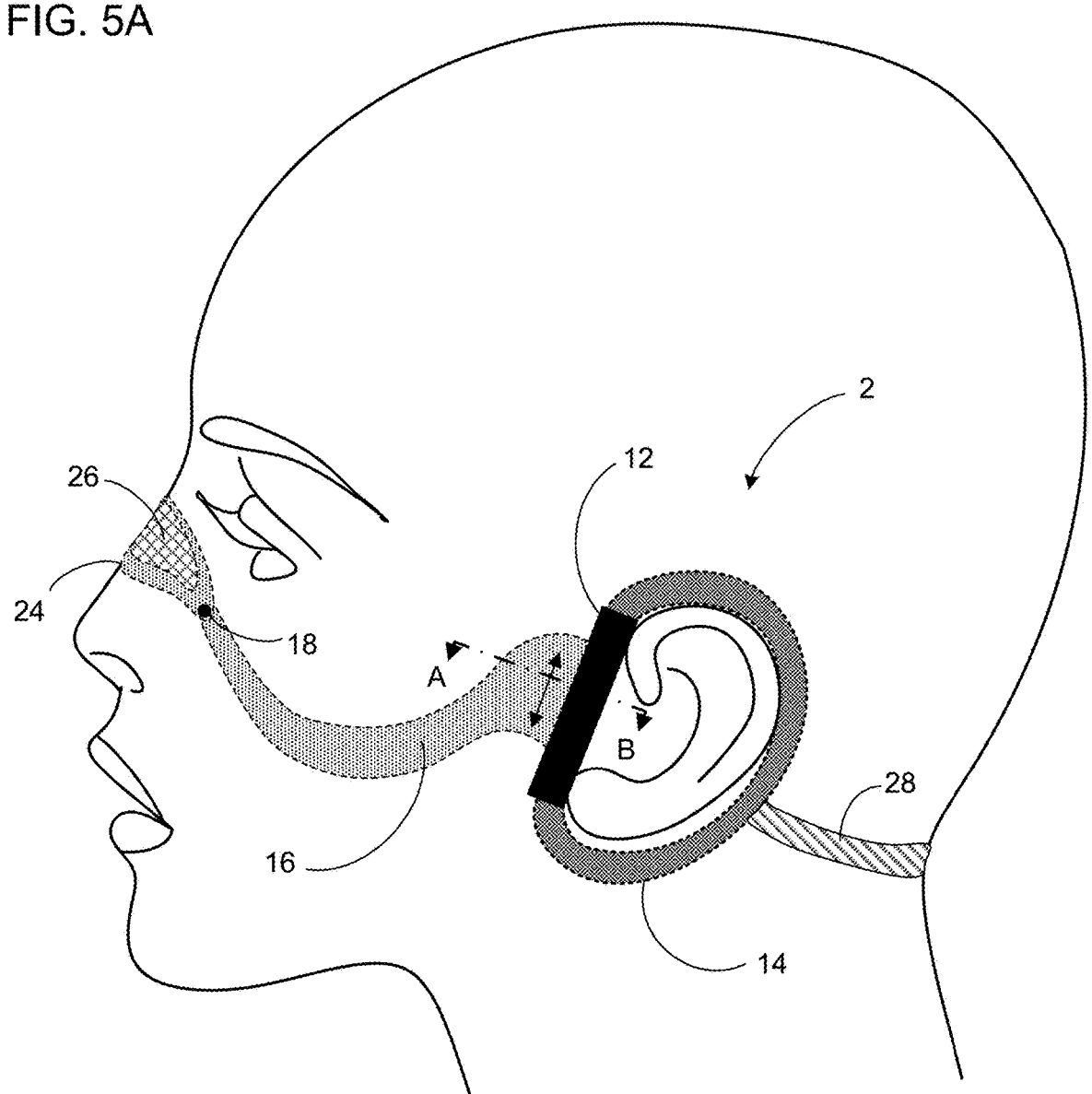
FIG. 5A represents a side view of a cheek positional support together with nose band and optional neck band according to an embodiment of the invention.
Figure 5B:
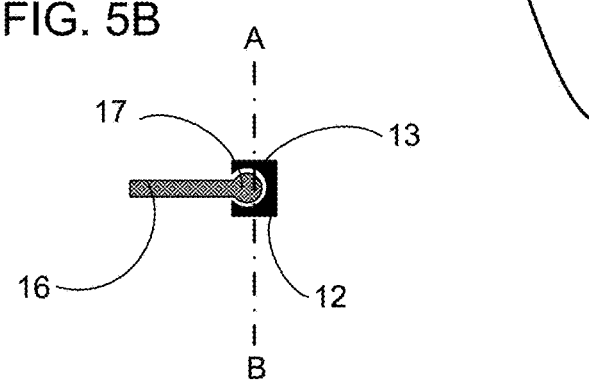
FIG. 5B depicts a cross section through the ear band showing an adjustable ear height mechanism.
Figure 6:
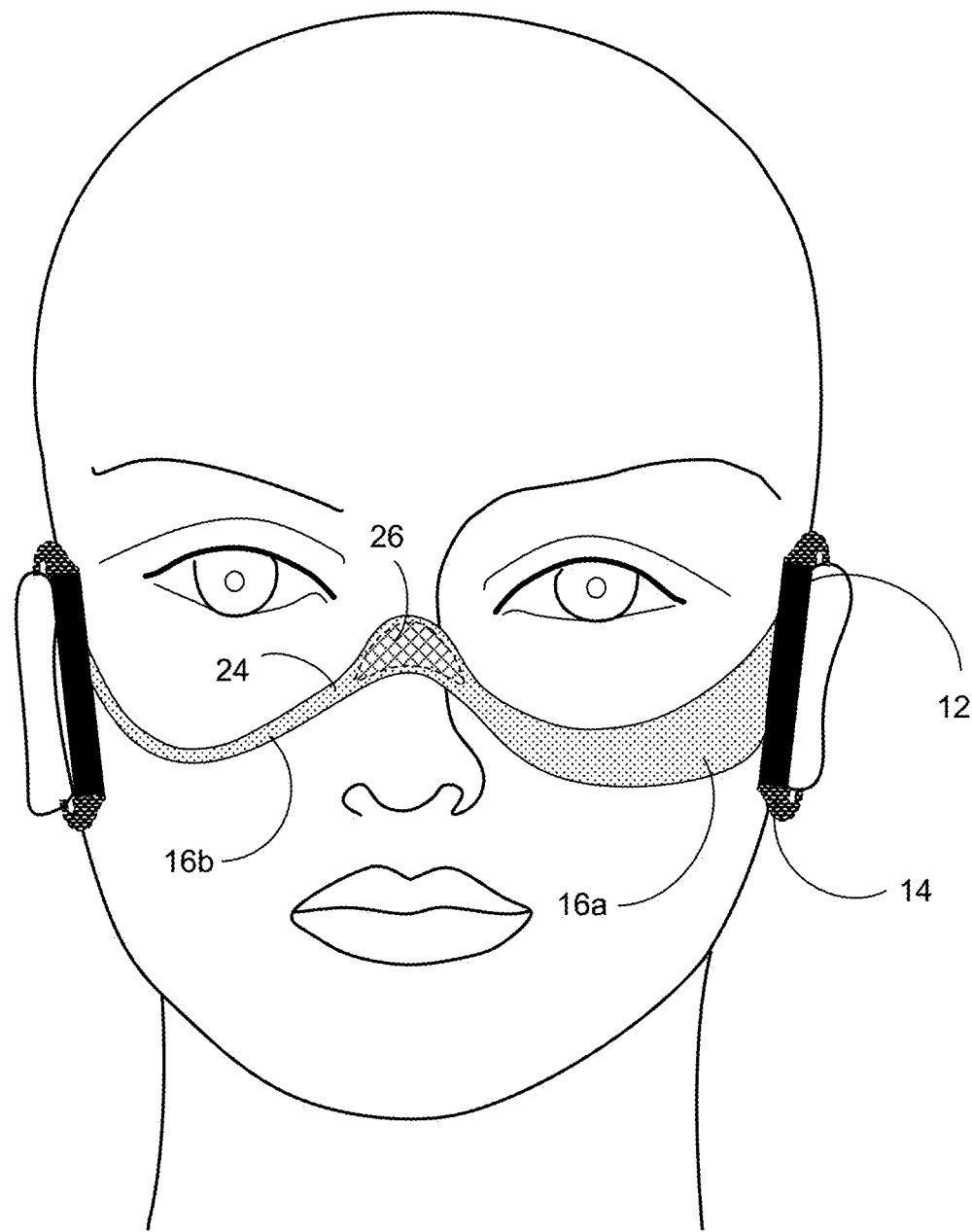
FIG. 6 represents a frontal view of cheek positional supports of various widths together with nose band.
Figure 7:
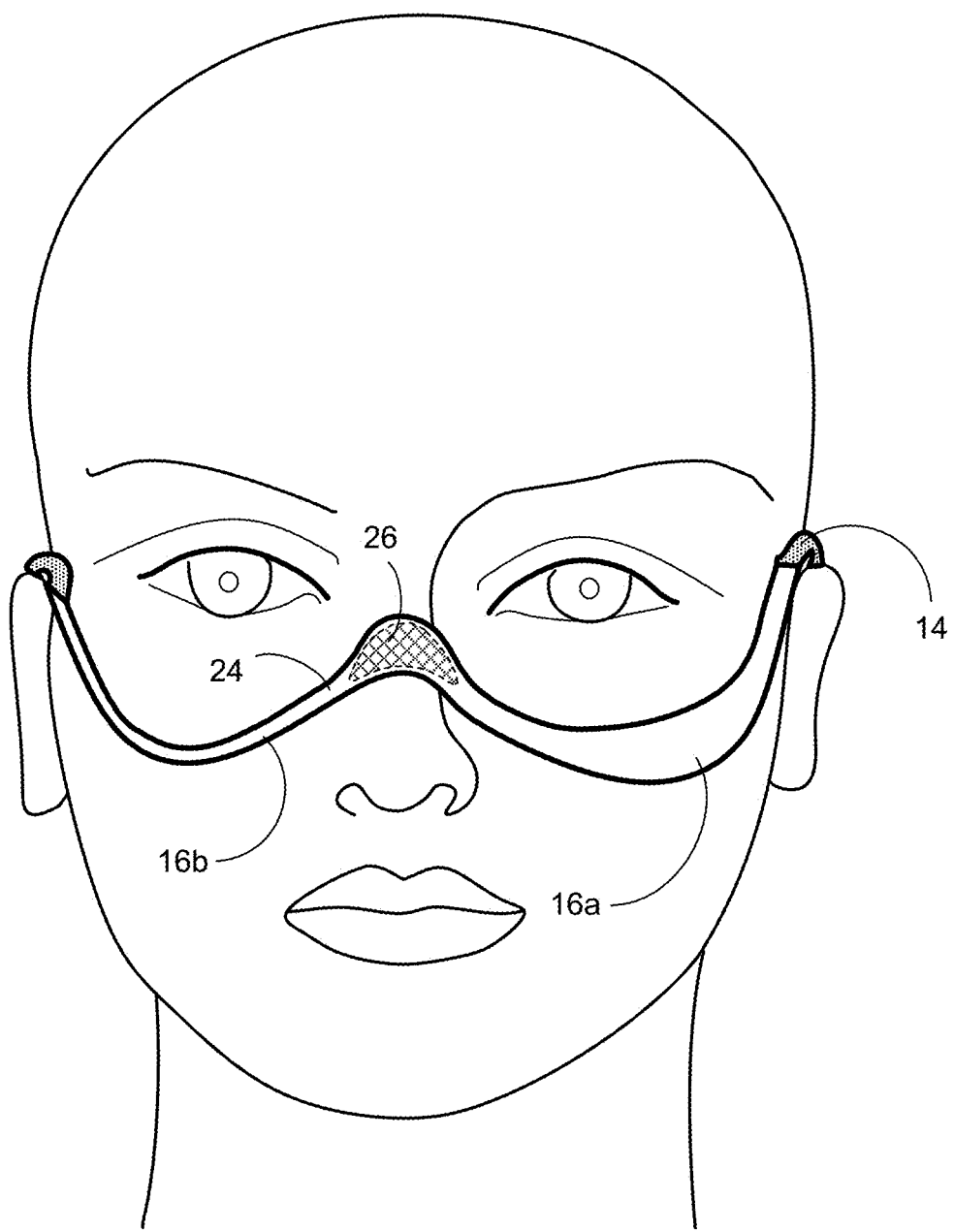
FIG. 7 represents a frontal view of another embodiment of cheek positional supports of various widths together with nose band and an ear strap that hooks over the top of the ear.

As depicted in FIG. 5, FIG. 6 and FIG. 7, the support device may be in the form of a silicone mask that has semi-rigid nose bridge structure. Cheek supports 16 are connected to one another by nose-bridge 24 that rises over the wearer's nose. Nose-bridge 24 preferably includes a semi-rigid nose structure 26 that is deformable to custom fit the nose of the wearer. For example, semi-rigid nose structure 26 may be a thin metallic or thermosetting plastic sheet that provides structure to the nose-bridge and allows the nose bridge to avoid application of undue pressure of the mask to the wearer's nose. Semi-rigid nose structure 26 may be internal or externally affixed to nose-bridge 24. If desired, nose-bridge 24 may be continuous with the material forming cheek support 16 and thus lacking any interconnecting piece or may have a releasable connector 18. If desired, and as optionally depicted in FIG. 5, support device 2 may include a back neck strap 28 connected to the ear strap 14 and thus ultimately to the outer portions of each cheek support 16 and extending around the wearer's head to provide the desired support pressure on facial structures. Back neck strap 28 provides further adjustment of the pressure of cheek, brow or chin supports by how tightly the strap is adjusted. The back neck strap can be in the form of two interconnecting straps that are connectable to one another by a Velcro type of connection, a buckle, or any other adjustable connection.

In one embodiment as depicted in FIG. 5A, bar 12 is a rigid structure that includes a channel. In such embodiments, the end of cheek support 16 that meets bar 12 includes a raised terminal portion 17 that can be slidably affixed within the channel 13 of bar 12. By moving the raised portion of cheek support 16 up and down bar 12 as shown by the double ended arrow, the device can be adjusted to the height of the patient's ears.

Figure 16A:
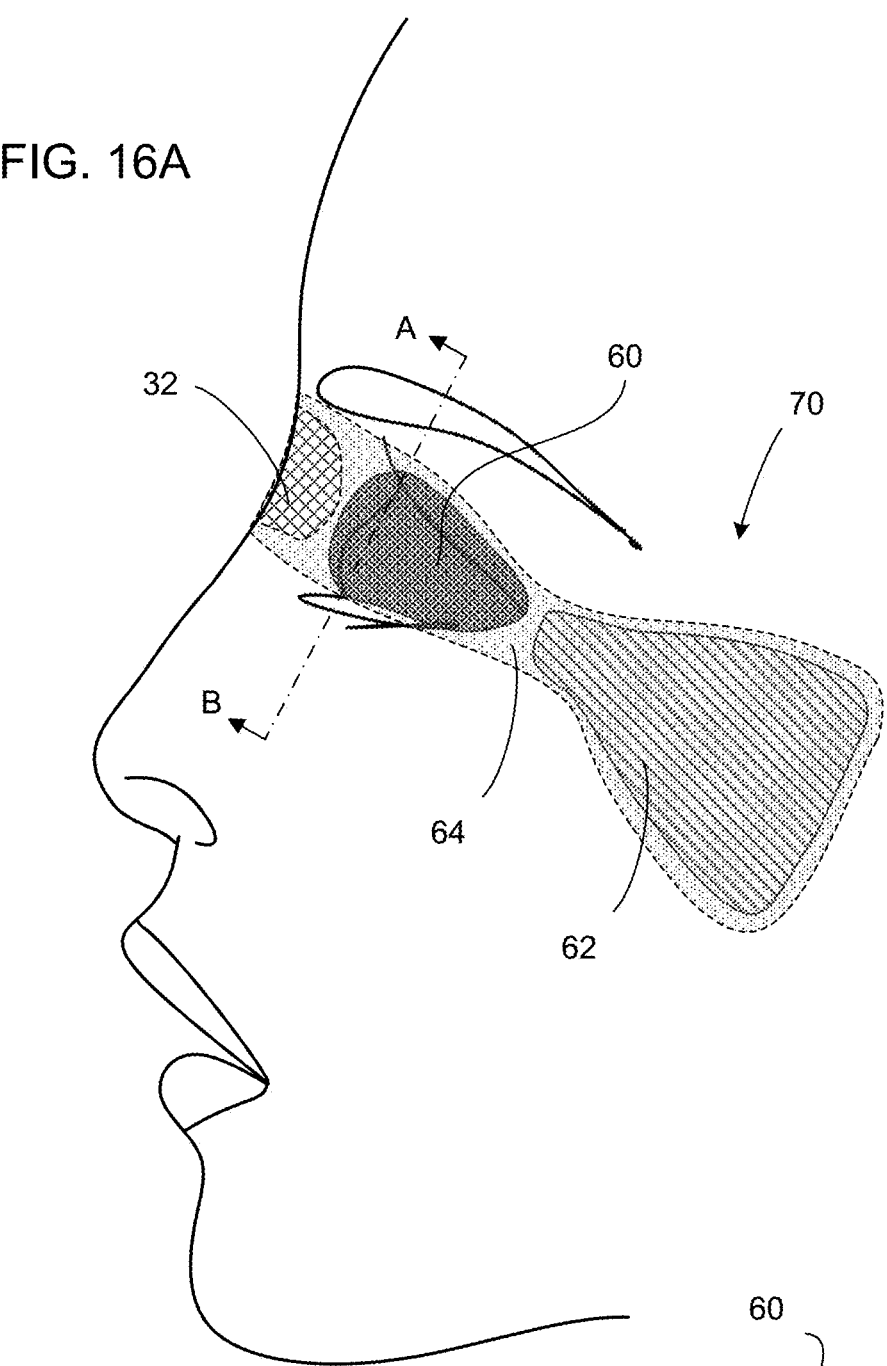
FIG. 16A depicts alternative embodiment of an eyelid closure device including a silicone gel pad over the eyeball.
Figure 16B:
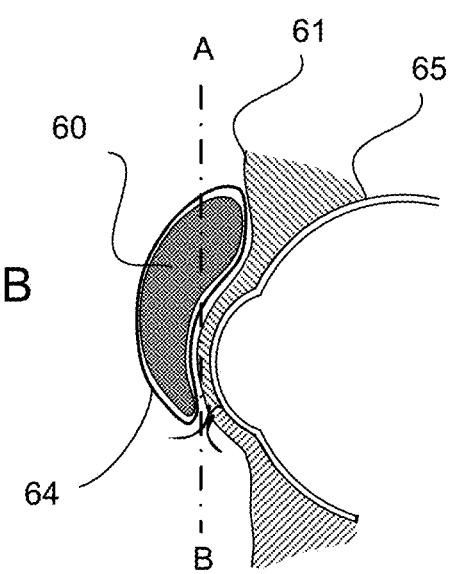
FIG. 16B depicts a side view cross-section through the indicated portion of FIG. 16A.

As depicted in FIG. 6 and FIG. 7, check supports may be thin as in FIG. 16B or relatively thicker as in FIG. 16B. Ear straps 14 may be provided that circle the ear as depicted in FIG. 6 or an ear piece that hangs on the ear may be utilized as depicted in FIG. 7.

Figure 8A:
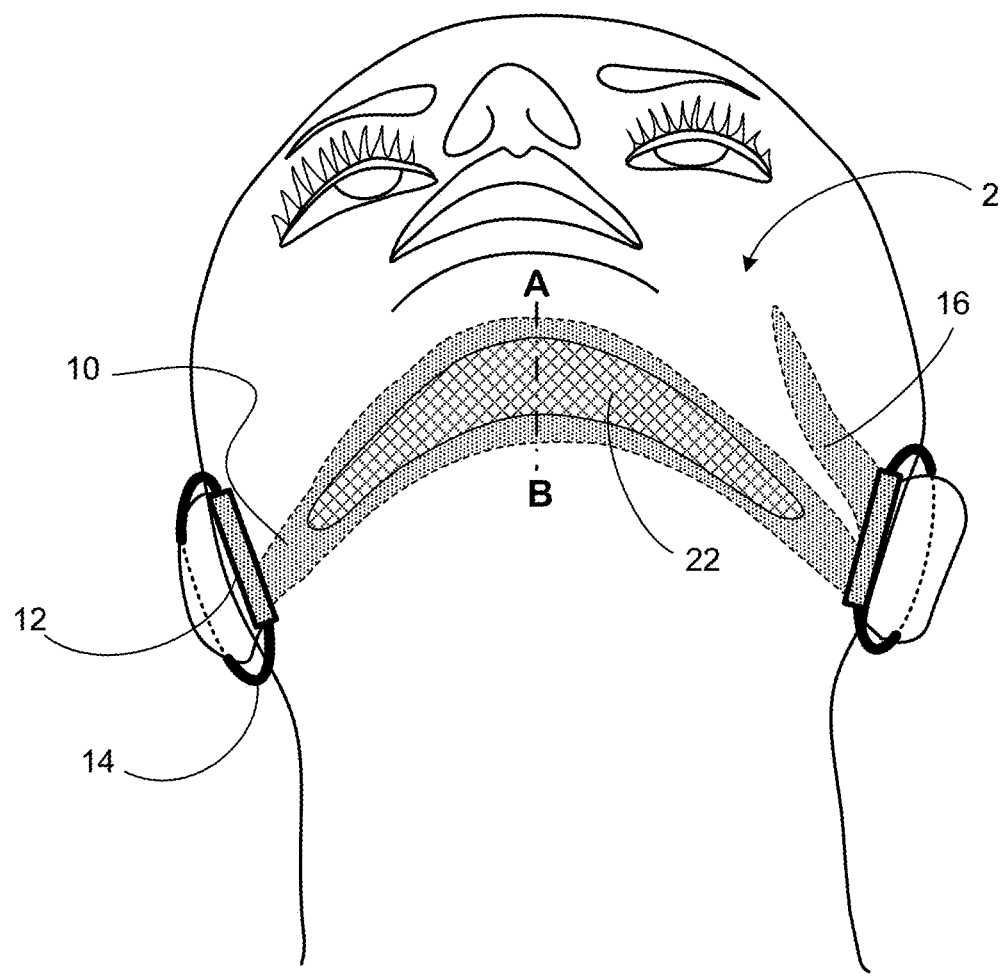
FIG. 8A represents an upward facing view of a chin positional support.
Figure 8B:
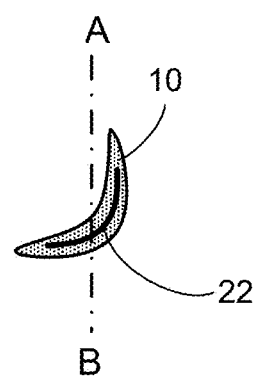
FIG. 8B represents a cross section of the chin support of FIG. 8A wherein an included rigid member is included.

With respect to a lower jaw or chin implant support, as depicted in FIG. 8A, the positional support device may be in the form of a sling 10 that extends from bar 12 and is held in place by ear strap 14. With respect to the chin implant support, the more structurally defined support area of the device may be attached to a back neck strap or straps such as depicted in FIG. 5 for holding the device in place to provide the desired stabilizing forces to the implant area. In the embodiment depicted in FIG. 8A, cheek support 16 includes a semi-rigid support armature 22 that can be molded to fit the user. The armature is shown in cross-section in FIG. 8B. As depicted on one side of the face of FIG. 8A, the positional support device may or may not include a cheek support 16.

Figure 9:
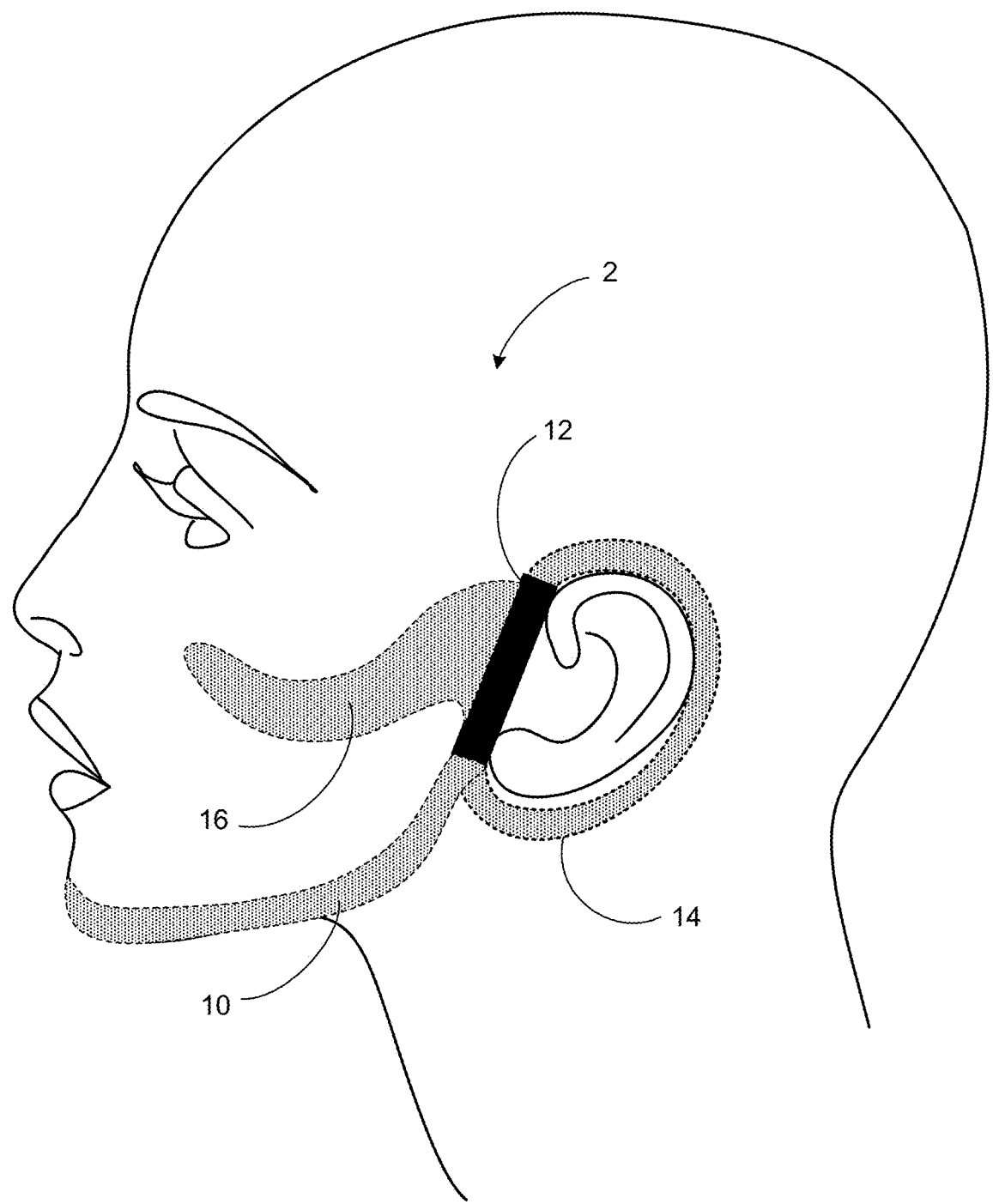
FIG. 9 represents a side view of a cheek positional support together with lower jaw support according to one embodiment.

As depicted in FIG. 9, support device 2 may be in the form of a combination of cheek supports 16 resting on and below surgical implants over the cheek bones. The cheek support 16 extends from bar 12 that is held in place by ear strap 14. In the embodiment depicted in FIG. 9, support device 2 further includes a lower jaw or chin implant support 10 that extends from bar 12 and is held in place by ear strap 14. With respect to the chin implant support, the more structurally defined support area of the device may be attached to a back neck strap or straps such as depicted in FIG. 5A for holding the device in place to provide the desired stabilizing forces to the implant area.

Figure 10:
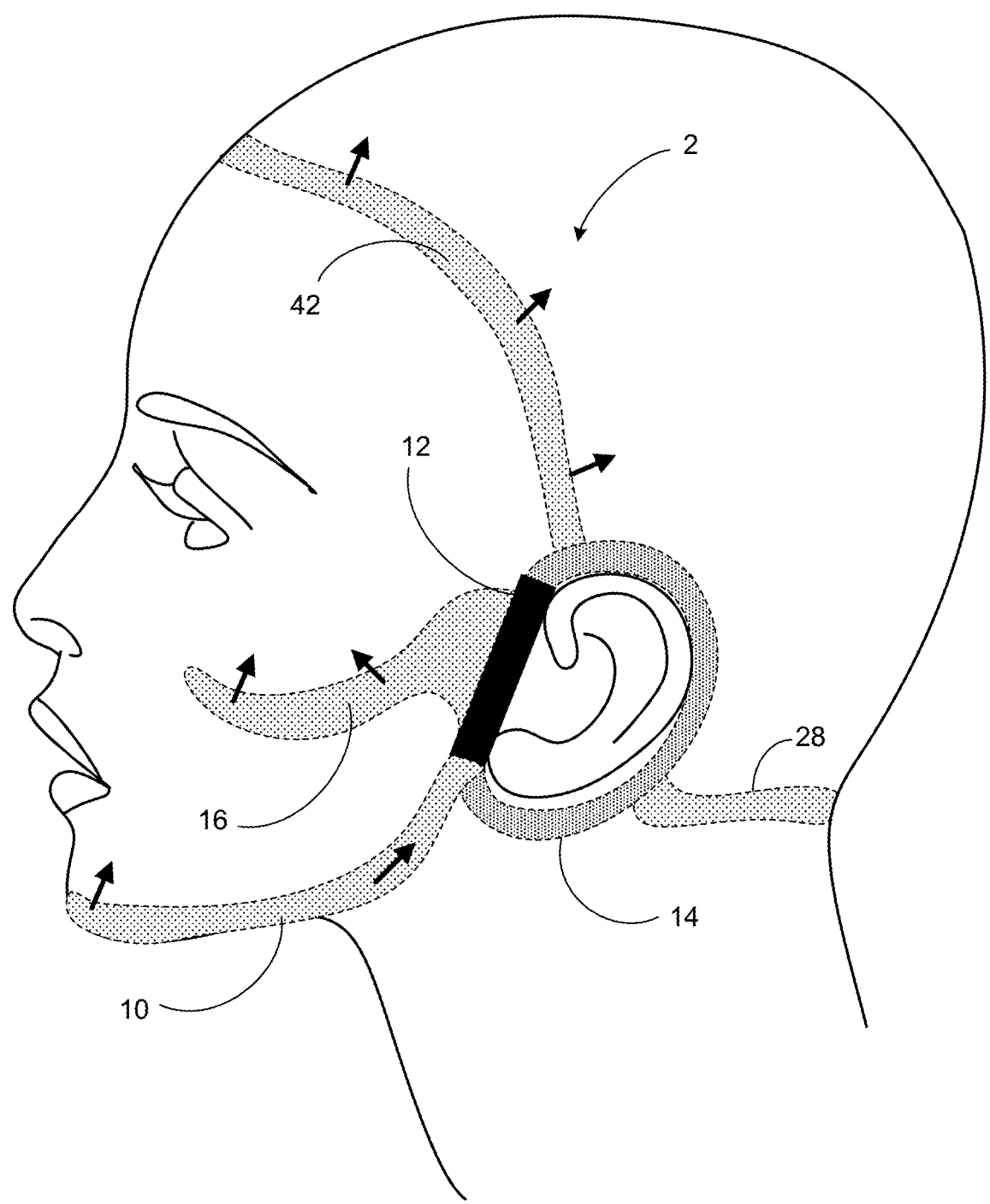
FIG. 10 represents an embodiment including cheek, chin and forehead supports.

In the embodiment depicted in FIG. 10, support device 2 includes cheek supports 16, a lower jaw or chin implant support 10, and brow support 42. The additional brow and chin supports may be tensionable by back neck strap 28 as previously described. Arrows depict the forces obtainable by aspects of the device. In one embodiment, each of the cheek, brow and chin supports are composed of silicone sheeting that is self-adhesive to the skin. The cheek, brow and chin supports may be manufactured into one integral unit with attachable ear straps or pieces or may include ear straps or pieces as part of the integral unit.

Figure 11:
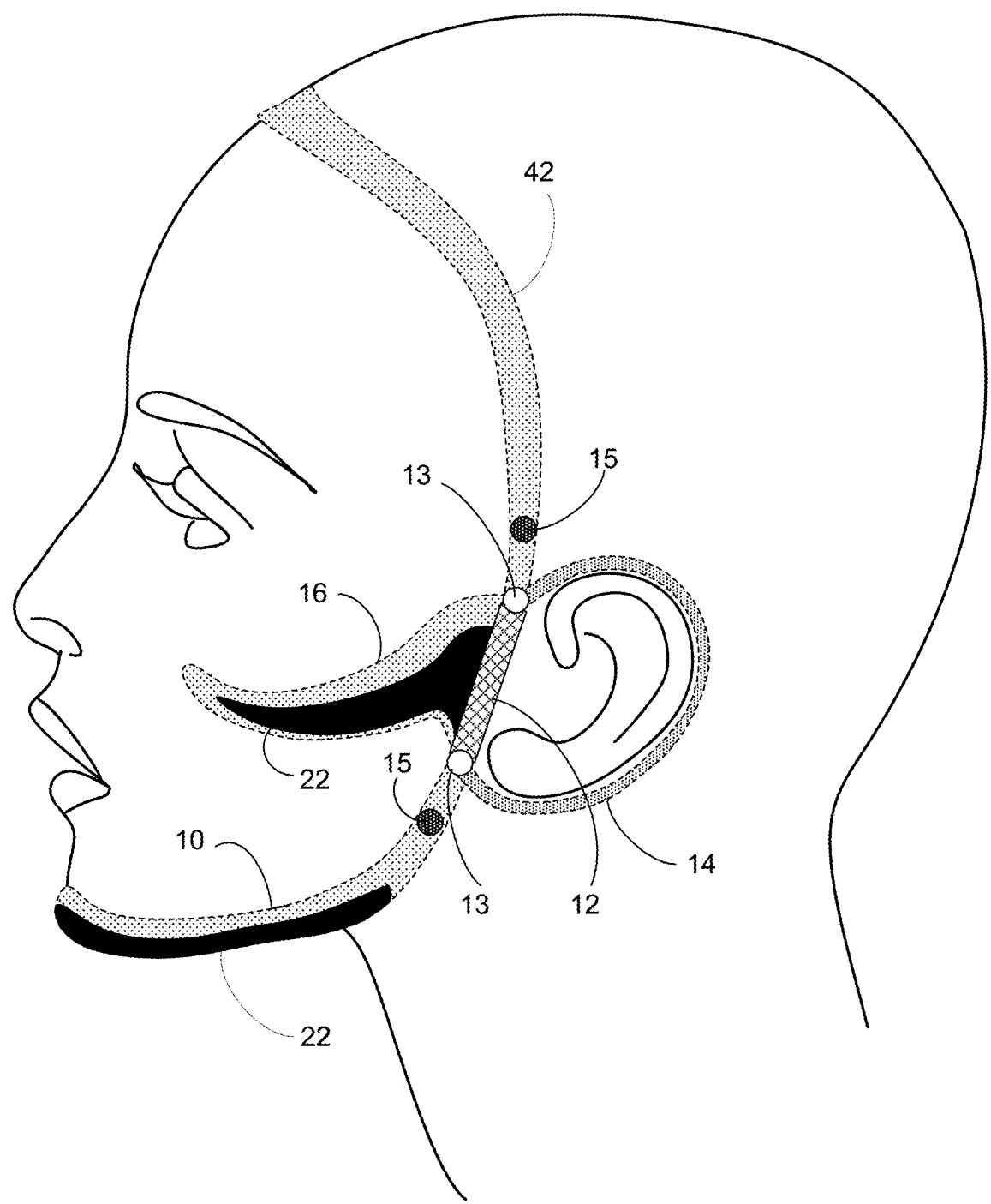
FIG. 11 represents an embodiment including cheek, chin and forehead supports including rigid support members.

FIG. 11 depicts an alternative embodiment wherein either or both of cheek support 16 and chin support 10 include semi-rigid support member 22 that is deformable to custom fit to the individual wearer. The semi-rigid support member 22 may be internal or external to the cheek or chin supports but is preferably not in contact with the skin. In the depicted embodiment, a version of ear band 14 is provided that is releasably attached at connectors 13, which can be a clasp, snap, button, hook and loop, cleat or other type of releasable connector. In certain embodiments, brow support 42 and/or chin support 10 include further attachment connector 15 connectable to the attachment member of connector 13 such that either the brow support or chin support can be shortened to fit the anatomy of the user. In one embodiment, connectors 13 are separated by bar 12, which may be rigid or semi-rigid. Where ear band 14 is a loop as depicted, the loop may be formed of a flexible material such as for example silicone sheeting or elastic fabric, or may be a relatively non-elastic strap, lace, rope or the like.

Figure 12A:
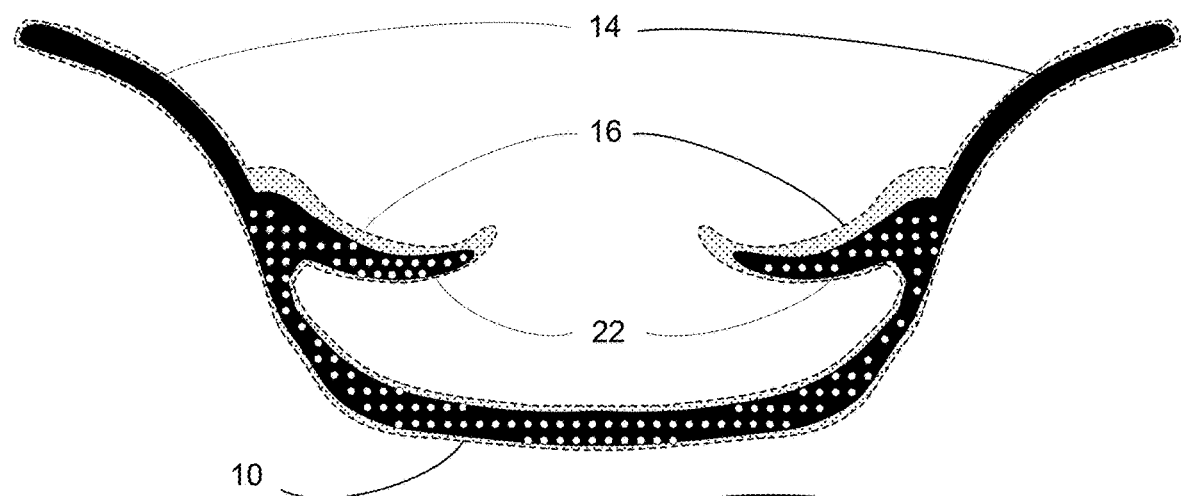
FIG. 12A depicts one embodiment of a chin and cheek support including a thermoplastic frame as supplied and before custom molding.

FIG. 12A depicts one embodiment of a chin and cheek support including a thermoplastic frame as supplied to the user before custom molding. In one embodiment the thermoplastic frame is encapsulated in medical grade silicone sheeting. The support unit may be supplied essentially flat. The user takes the essentially flat support and applies heat such as in a bath of hot water. Once the thermoplastic is sufficiently heated, the support is applied to the face. The chin support 10 is molded to the fit the contours of the jaw while cheek support 16 is molded to the cheek contours by manipulation of the thermoplastic frame 22 against the structures of the chin and cheek. Ear pieces 14 are pulled and fitted around the ear to provide desired tension on the chin and cheek supports. As depicted in FIG. 12A, the included thermoplastic frame is perforated for ease in pulling and molding to the shape of the face.

Figure 12B:
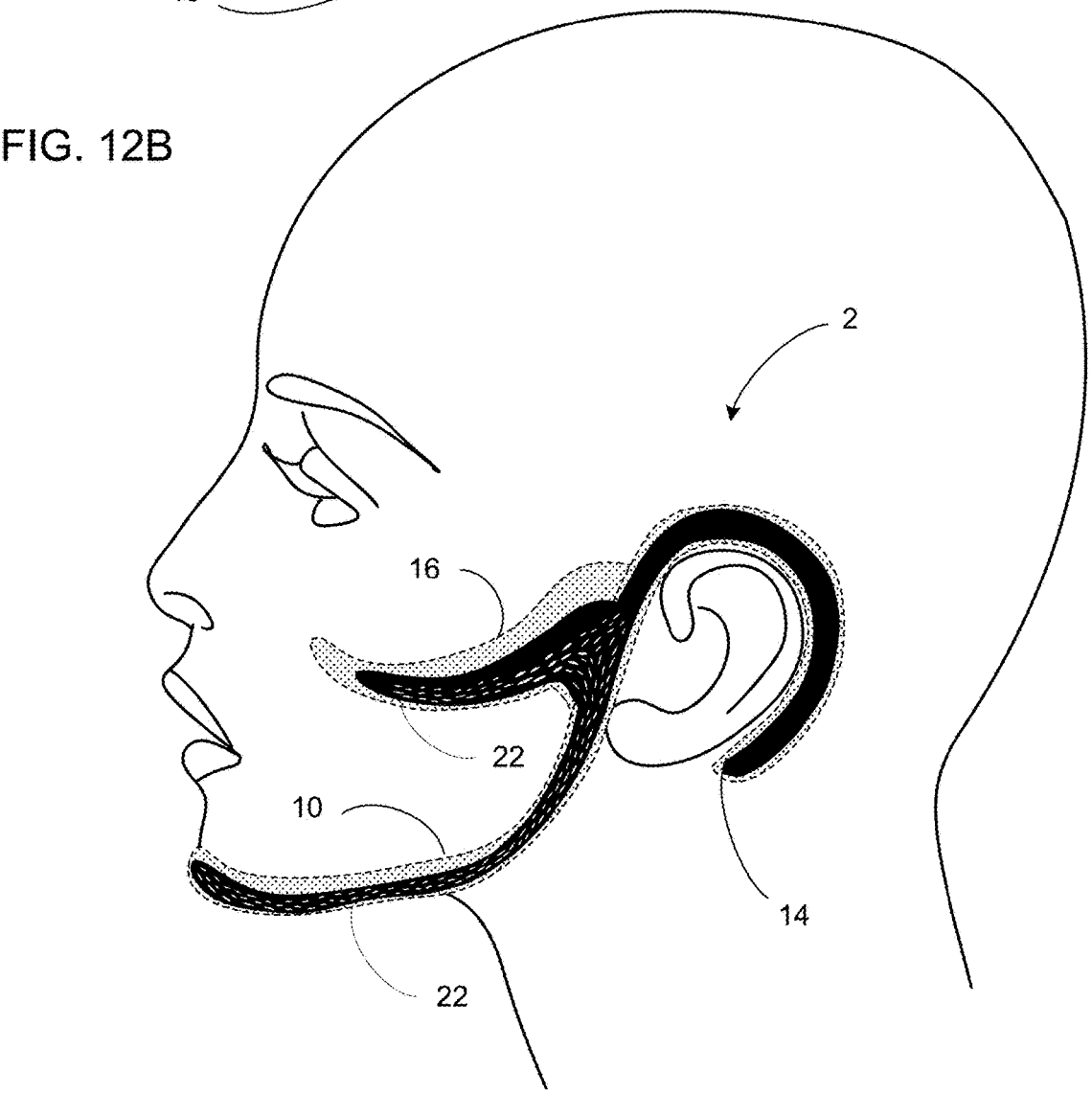
FIG. 12B depicts a side view of the embodiment of FIG. 12A after custom fitting.

FIG. 12B depicts a side view of the embodiment of a FIG. 12A after custom fitting. As depicted, the original perforations of FIG. 12A are deformed as the thermoplastic is molded to the shape of the face. In certain embodiments the support 2 lacks cheek supports and chin support only is provided.

Figure 13A:
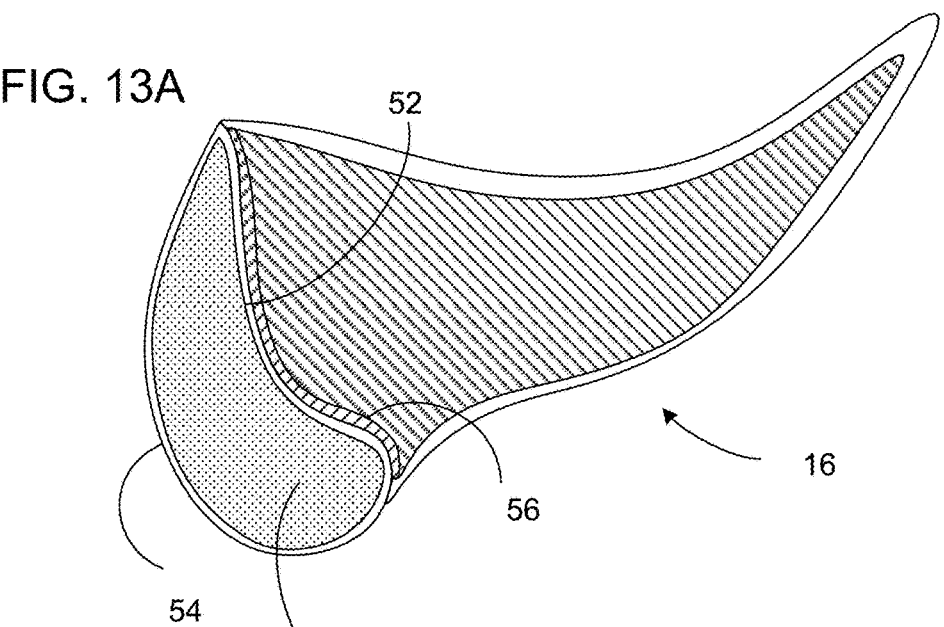
FIG. 13A depicts a cross section of an embodiment of a cheek support including an adhesive layer disposed across substantially the entire skin facing surface.
Figure 13B:
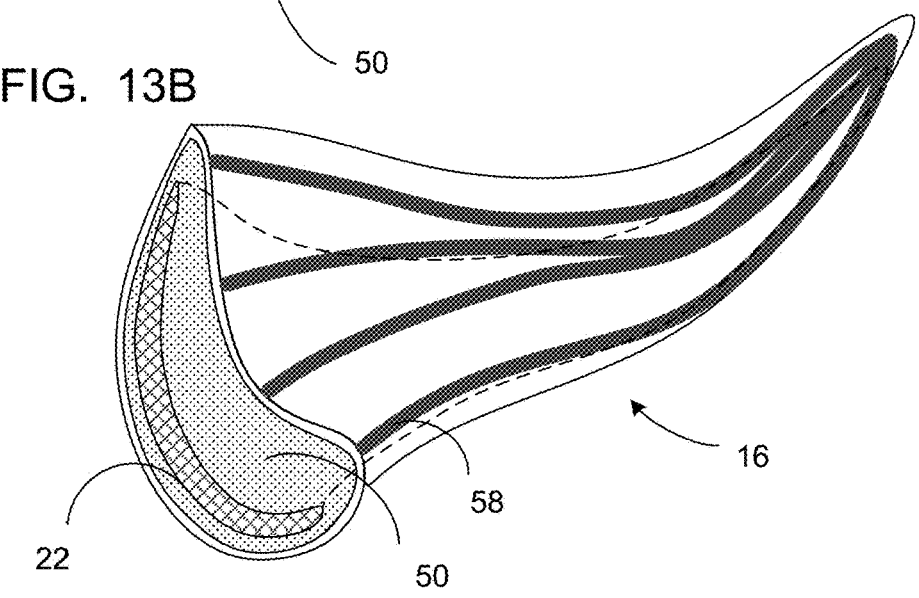
FIG. 13B depicts a cross section of an embodiment of a cheek support including adhesive strips over a portion of the skin facing surface and including a rigid support member.

FIG. 13A and FIG. 13B depict cross-section of tear drop shaped cheek supports according to certain embodiments. In the depicted embodiments of FIG. 13A and FIG. 13B, the cheek support has a slightly concave inner layer 52 that faces the skin and an opposite facing outer layer 54. Inner layer 52 is sealed to outer layer 54 thereby encasing silicone gel material 50. In one embodiment the cheek support is designed to be barely perceptible and thus inner and outer layers 52 and 54 are formed of a clear plastic material such as polyurethane and the silicone gel is colorless or skin toned. The tear drop shape of the cheek support is established during manufacture through molding and curing of the silicone gel into the desired shape. One such curing method is described in Chang U.S. Pat. No. 5,693,164 and silicone bras have been developed that include silicone gels encased in elastomeric plastic membranes such as described in Chen U.S. Pat. No. 6,758,720. In the depicted embodiment of FIG. 13A, the skin facing surface of cheek support 16 is largely covered by reusable adhesive layer 56. In certain embodiments, the inner layer 52 and outer layer 54 are a polyurethane material that encloses a silicone gel. Inner layer 52 is further coated or manufactured with further innermost layer 56, which is releasably adhesive to the skin. In other embodiments, inner layer 52 and adhesive layer 56 are the same. As used herein, "adhesive layer" means any layer that provides a releasable adhesion to the skin of the user such that the positional support does not slip from its desired position but may be easily removed without damage to the skin. The reusable adhesive layer 56 may be a layer of silicone cured sufficiently to retain its shape while retaining adhesive properties. Such silicone strips are currently used in undergarments to reduce slipage.

In the depicted embodiment of FIG. 13B, the skin facing inner surface of cheek support 16 is arrayed with adhesive strips 58. Alternatively, the adhesive material may be arrayed in drops over the inner surface. In the embodiment depicted in FIG. 13B, cheek support 16 includes an internal semi-rigid support armature 22 that can be of a fixed shape or can be designed to be molded to fit the user.

Figure 13C:
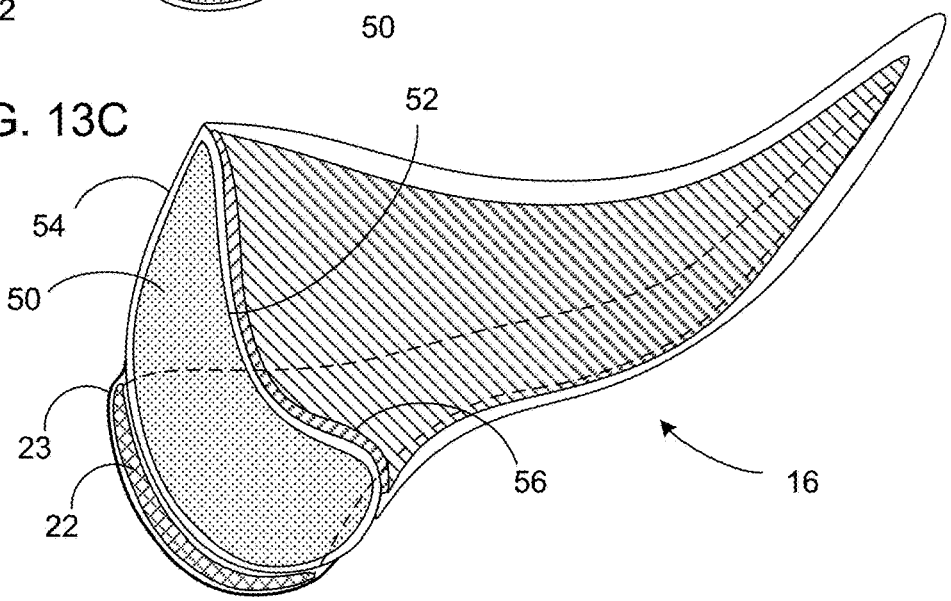
FIG. 13C depicts a cross section of an embodiment of a cheek support including a rigid support member that is disposed in an outer pocket.

In the depicted embodiment of FIG. 13C, cheek support 16 includes a semi-rigid support armature 22 that is fit into an outer sleeve or pocket that is formed with or affixed to outer layer 54.

Figure 14:
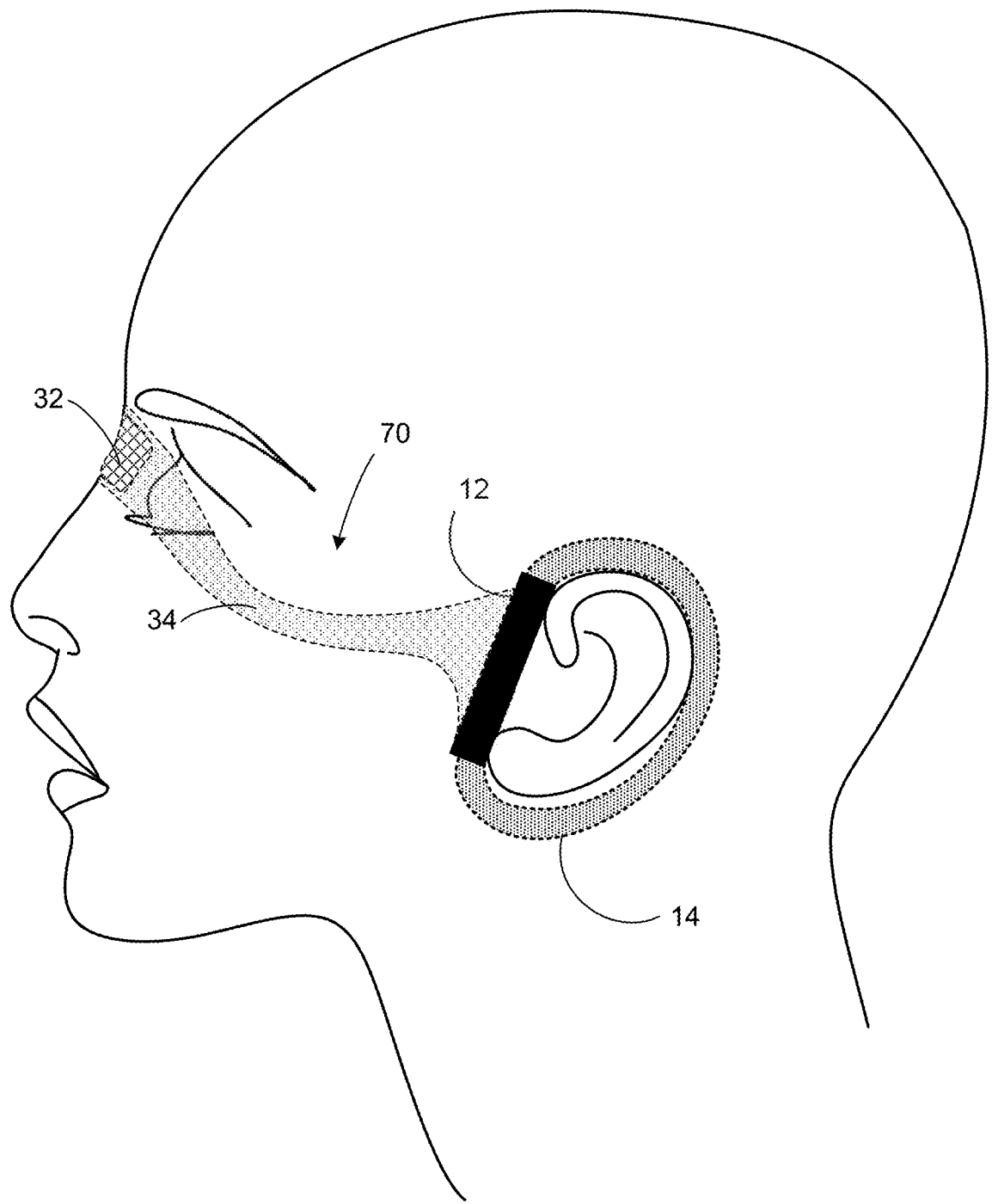
FIG. 14 represents a side view of an eyelid closure device according to one embodiment.

In the embodiment disclosed in FIG. 14, an eyelid positional device 70 is provided that enables gentle closure of the eyelids. In certain diseases such as Grave's opthalmopathy, the eyelids retract during sleep and corneal drying and erosion may result. Currently such events are controllable by taping the eyelids which renders the wearer unable to quickly adapt to the need for sight and may result in sensitivity to the tape adhesives. Alternative goggles having a strap around the back of the head results in a cumbersome device that is easily dislodged during sleep. Provided herein in one embodiment is an apparatus that provides gentle closing tension to the eyelids while enabling easy removal by pulling off an ear strap 14 over the ear. In the depicted embodiment, flexible band 34 includes a semi-rigid nose bridge 32 that is deformable to custom fit the nose of the wearer. As previously described, semi-rigid nose bridge 32 may include a thin metallic or thermosetting plastic disc or strip that is deformable to custom fit the individual patient. Semi-rigid nose-bridge 32 may be internal or externally affixed to flexible band 34. The rigid or semi-rigid aspect of the nose bridge is relatively short such that the flexible band 34 takes off approximately half-way across the full depth of the bone of the nose at the region of the inner tear duct. Thus, pressure against the eye ball is minimal as flexible band 34 extends across the cheek to meet the ear strap 14. Ear strap 14 may include a rigid member such as depicted bar 12. Alternatively, ear strap 14 may be entirely flexible and contiguous with flexible band 34. In a further embodiment, an ear piece such as that depicted as ear piece 15 in FIG. 4C or the ear piece including earbud 96 of FIG. 17A may be utilized. In one embodiment, flexible band 34 is formed of medical grade silicone or utilizes medial grade silicone gel sealed in a chamber between flexible sheets. In other embodiment, flexible band 34 may utilize other flexible and stretchable compositions known to those of sill in the art including but not limited to flexible woven fabrics and neoprene. In one embodiment, flexible band 34 is formed of a woven fabric material and the skin facing surface includes zones including silicone arrayed in strips or spots to provide slip resistance. The silicone is deposited on and bonds to the fabric by coating or other deposition.

Figure 15A:
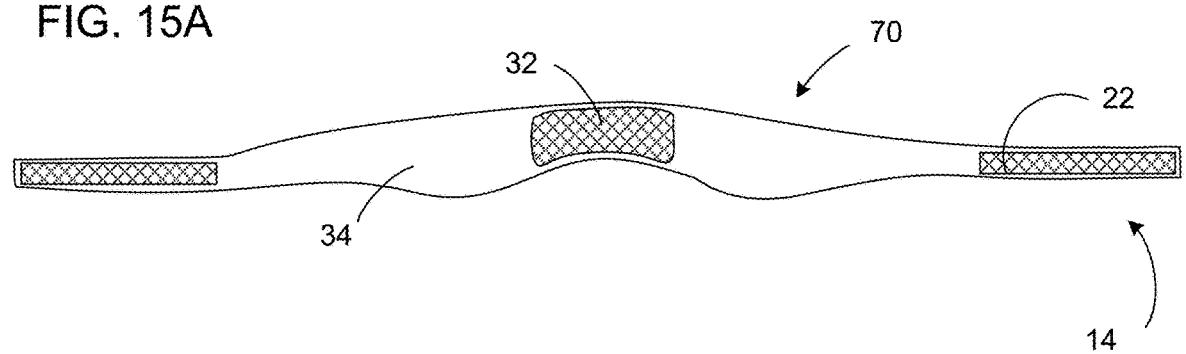
FIG. 15A depicts one embodiment of an eyelid closure device including a moldable structure in the nose bridge and ear strap as supplied and before custom molding.
Figure 15B:
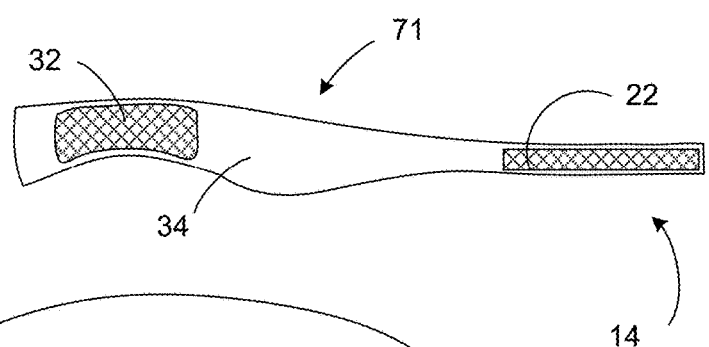
FIG. 15B depicts one embodiment of a single eyelid closure device including a moldable structure in the nose bridge and ear strap as supplied and before custom molding.

FIG. 15A depicts one embodiment of an eyelid closure device 70 including a moldable semi-rigid nose bridge 32 and ear strap 14 as supplied and before custom molding. As described in reference to FIG. 12, the closure device may be supplied essentially flat as shown in FIG. 15A. In the case of devices including thermoplastic moldable nose bridge and ear strap elements, the user takes the essentially flat device and applies heat such as in a bath of hot water. Once the thermoplastic is sufficiently heated, the support is applied to the face. Alternatively, where moldable nose bridge 32 and ear straps 14 include internal moldable metal "skeletal" supports, the device is custom fit by bending the metal to fit. The nose bridge 32 is molded to the fit the contours of the nose by manipulation of the moldable frame against the bridge of the nose. Ear pieces or straps 14 are pulled and fitted around the ear by virtue of moldable armature 22 to provide desired tension across the eyelids. Ear straps 14 are similarly custom fit. FIG. 15B depicts one embodiment of a single eyelid closure device 71 including a moldable semi-rigid nose bridge 32 and ear strap 14 as supplied and before custom molding. The disclosed single eyelid closure may be utilized in lieu of uncomfortable eyepatches or compression taping where it is desirable to keep a single eye closed for healing of surgical procedures on the eye. Whether for one or both eyes, the silicone gel pad 60 depicted in FIG. 16A may be included in the eyelid closure devices of FIG. 15.

Figure 15C:
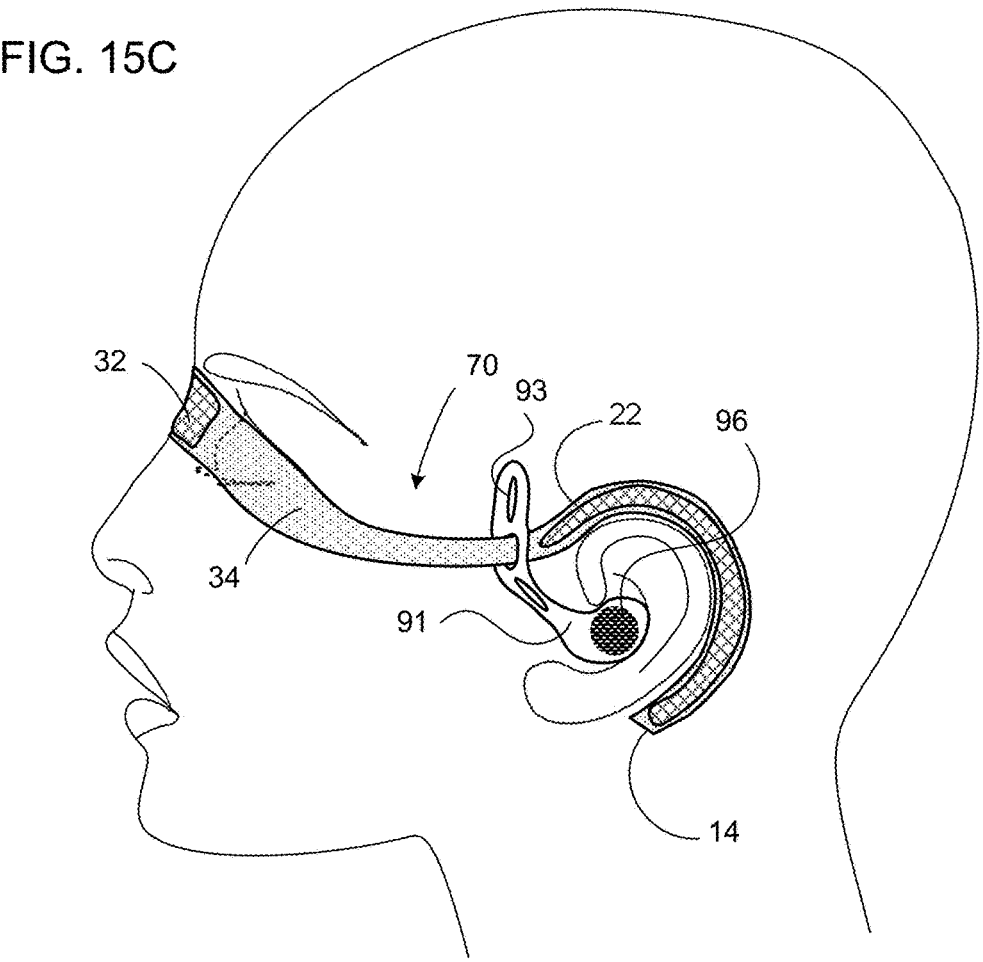
FIG. 15C depicts a side view of the embodiment of FIG. 15A or FIG. 15B after custom fitting.

FIG. 15C depicts a side view of the embodiment of FIG. 15A or FIG. 15B after custom fitting. In certain embodiments, the eyelid closure device may be supplied with adjustable ear bud halter 91 that connects eyelid closure device body 34 to ear bud 96. Inclusion of an ear bud provides considerable stability to the device and provides an added advantage in ambient noise mitigation. Adjustable ear bud halter 91 may be affixed to eyelid closure device body 34 by a number of alternative affixation method including hook and loop attachments, snaps, buttons, etc. In the depicted embodiment ear bud halter 91 includes a series of openings 93. The relative position of the eyelid closure device body 34 is adjustable up and down by selecting the appropriate opening 93 through which the device body 34 is affixed.

FIG. 16A depicts an alternative embodiment of an eyelid closure device 70 including a moldable structure in the nose bridge 32 that affixed to eyelid closure device body 64. The moldable structure may be disposed over, under or within the device body. In certain embodiments the device body is composed of a silicone sheet. In the depicted embodiment, silicone gel pad 60 is included in eyelid closure device 70 and, via a concave inner shape, conforms to and pads the eyeball and has a tissue like feel. In one embodiment the silicone gel is a soft, essentially sticky material that is encased between inner and outer sheets that form an enclosing casing 64 as shown in FIG. 16B. Underlying adhesive pad 62 is affixed to or is integral to the device body and is adapted and dimensioned to adheres a distal aspect of the elastomeric skin to the upper cheek or temple area.

As depicted in FIG. 16A and FIG. 16B, the eyelid closure device 70 may, if desired, be worn across the eyelid either short of the eyelashes or may extend across the eyelashes. FIG. 16B shows a side view of an aspect of the lid closure device of FIG. 16A wherein silicone gel pad 60 overlies the closed upper eyelid 61 and conforms to the shape of the underlying eyeball 65. As with the embodiments depicted in FIG. 15A-FIG. 15C, the self-adhesive embodiments of FIG. 16A and FIG. 16B may be provided as single or double eye versions or one eye can be trimmed from a double eye version to provide a single eye patch including the full nose bridge. For single eye patch versions, an adhesive may be provided under the nose bridge to hold it securely in place.

FIG. 17A depicts one embodiment in which a positional support is provided that includes separate cheek supports 16 and upper mandible supports 11. Because the cheek and mandible supports are separately affixed to ear support attachment 90, either may be used without the other or both may be used together. It is noted that for purposes of this application reference to a chin support includes support for any structure of the mandible. In some indications such as that depicted, an upper mandible support is provided that delivers gentle tension over the masseter muscles overlying the gonial angle of the mandible. The positional supports may be applied before bedtime or rest to support facial structures during rest but may also be utilized during other activities such as exercise and may be further applied for stabilizing structures after surgery. The gentle tension and direct pressure provided by the device acts to retain a desirable position of underlying facial structures and counteract the effect of gravity that gradually result in sagging and the appearance of aging. Where facial implants exist, the cheek support controls the movement of the implants in the originally desired position by application of gentle pressure. As can be seen in the cross sections of FIG. 17B and FIG. 17C, the cheek and mandible supports include an inner soft silicone gel pad 84 disposed within casing 86 that provides gentle direct positional pressure against the skin and thus the underlying structures. Check support 16 includes semi-rigid support armature 22 while mandible support 11 includes support armature 82.

In certain embodiments, the two cheek supports and/or two mandible supports are affixed to one another by a connector 102 across a ventral aspect of a person's face (i.e. the nose or chin) that is releasably affixed to the supports by fastener 18. The fastening mechanism may be a hook and loop attachment, snap, button, or other releasable fastener and may be designed as a series of fasteners wherein selection of a given fastener determines the tightness of the connector. In the depicted embodiment, connector 102 is includes a central moldable structure 104 that can be custom fit over the bridge of the nose or around the chin. For example, central moldable structure 104 may be a thin metallic or thermosetting plastic sheet that provides structure to the nose bridge or chin strap and allows adequate fitting of the device without undue pressure across the nose or chin. The central moldable structure may be internal or externally affixed to the connector. In certain embodiments connector 102 is formed of an elastomeric material such as silicone. Use of connector 102 allows greater tension to be placed on the positional supports. In certain embodiments separate connectors are provided for going across the nose and around the chin while in other embodiments a single connector is provided that can be used in either location.

In the embodiment depicted in FIG. 17A, upper positional cheek support 16 and/or upper mandible support 11 are releasably affixed to ear support attachment 90. Ear strap 14 is affixed to ear support attachment 90 from which ear bud 96 depends. Addition of ear buds to the ear support provides considerable stability to the device and provides an added advantage in ambient noise mitigation. In certain embodiments sound delivery is provided through the ear buds when attached to a sound source or via a micro wireless receiver affixed to an element of the ear attachment structure.

The ear support attachment 90 can be provided with various attachment mechanisms two of which are depicted. In the cross section of FIG. 17B, the attachment is via a hook and loop attachment. As depicted a sheet of hooks 94 is affixed to the cheek and mandible supports while the corresponding loops 92 are affixed to ear support attachment 90. The order of hook and loop can be reversed with the loops on the cheek and mandible supports and the corresponding hooks on the ear support attachment. In the depicted embodiment, cheek support 16 and mandible support 11 include semi-rigid support armatures 22 within outer casing 86. Alternatively, the armatures may slide into a sleeve formed on the outside of the positional supports as depicted in FIG. 13C.

In the cross section of FIG. 17C, the attachment is via one or more locking slots 100 disposed in the ear support attachment 90 that engages catch-up pins 101. As depicted, an outer disk or plate 98 is disposed on each end of the catch-up pins 101 to hold the catchup-pins in the ear support attachment 90. The positional supports 16 and 11 can be adjusted up or down by sliding the catch-up pins up or down in the locking slot(s) 100.

As with previously discussed embodiments the inner skin facing layer of the positional supports may be provided with a releasable and reusable adhesive or may be comprised of a self-adhesive compound or coating.

Figure 18:
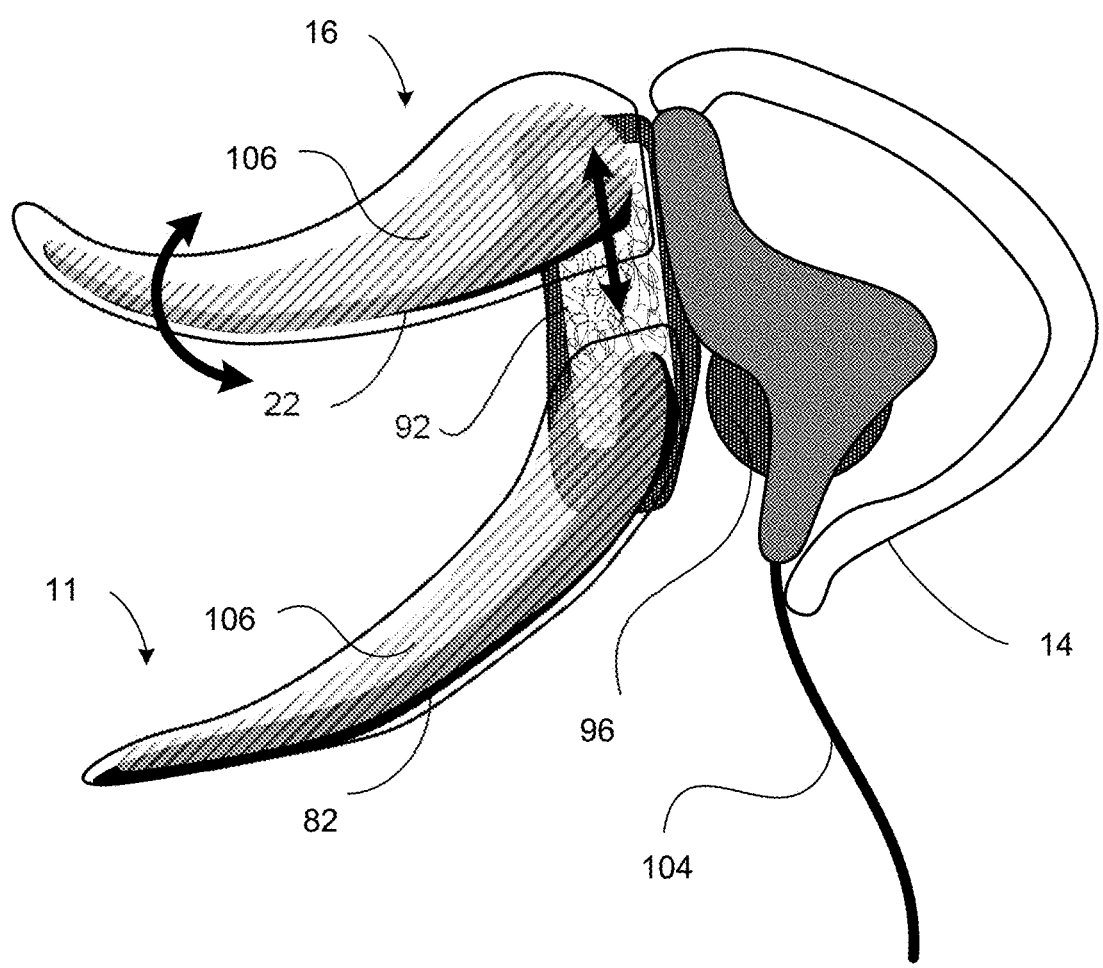
FIG. 18 depicts another embodiment of an ear piece including a stabilizing ear bud and attachment to separate cheek and mandible supports.

FIG. 18 depicts another embodiment of an ear piece 14 including a stabilizing ear bud 96 and attachment to separate cheek and mandible supports. The depicted embodiment shows the ear piece with a connector 104 to a sound source. The extent of the included silicone gel pad is shown as the hatched lines 106 in each of the cheek support 16 and mandible support 11. By virtue of the depicted hook and look attachment (loop aspect 92 is showing), the cheek and mandible supports can be moved up and down but can also be rotated for ideal positioning as shown with the thick arrows.

Figure 19:
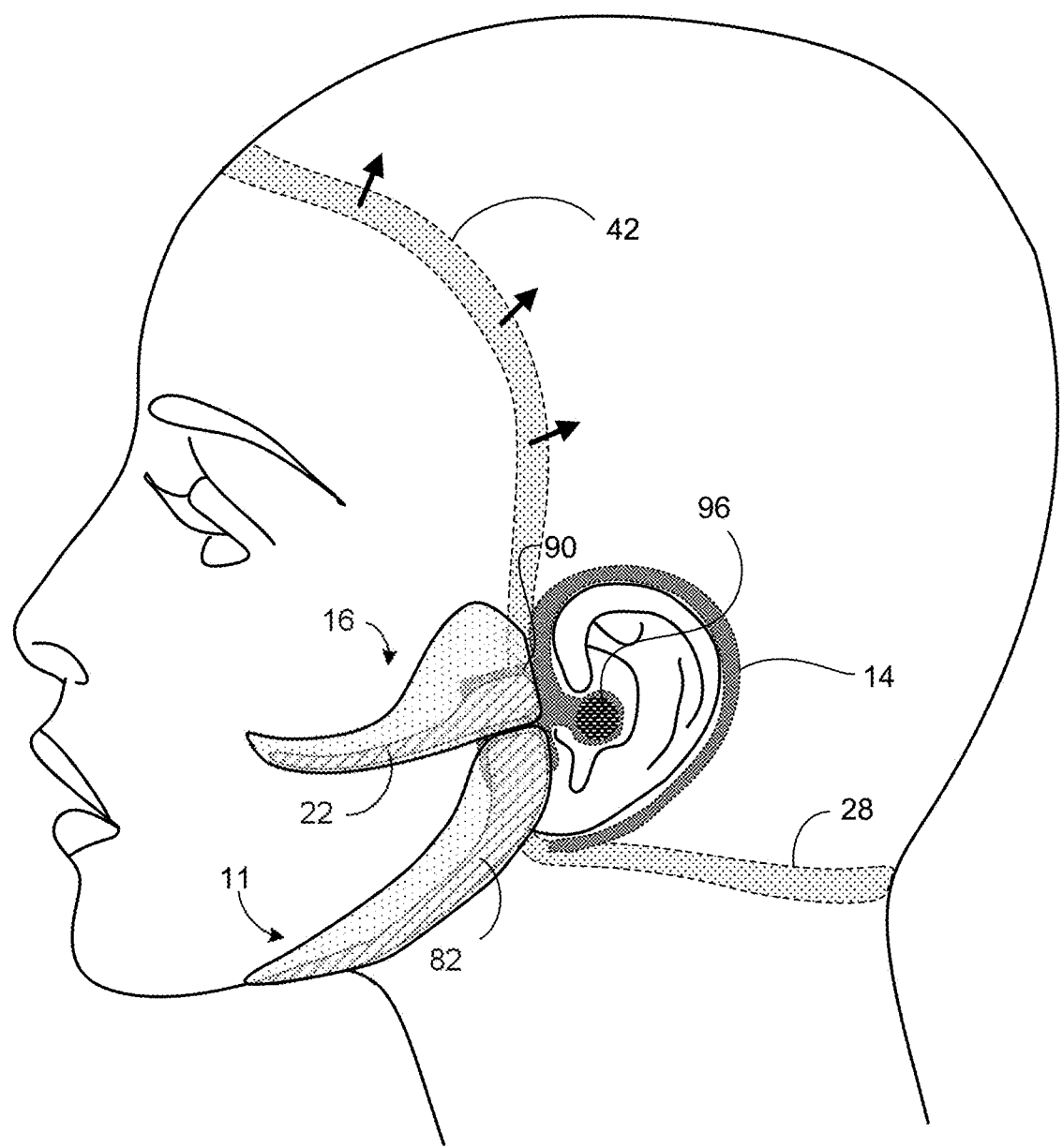
FIG. 19 depicts another embodiment of a chin and cheek support including an ear piece secured by an ear bud and a forehead support.

FIG. 19 depicts another embodiment of an upper mandible support 11 and cheek support 16 including an ear piece 14 secured by an ear bud 96 and a forehead support 42 that is attached to ear support attachment 90 and is secured to back neck strap 28. In one embodiment, the forehead support 42 and back neck strap 28 are adjustable and can be tightened to provide the desired leverage to the cheek and/or mandible supports. Cheek support 16 includes semi-rigid support armature 22 while mandible support 11 includes support armature 82. Each of the mandible and cheek supports include a silicone gel pad that provides downward pressure onto underlying tissues.

In one embodiment, a mold is taken of the patient's face using a thermosetting plastic mask blank such as of the type used for radiation treatment positioning. Such masks are described in Ungemach, U.S. Pat. No. 7,290,548, disclosed herein by reference, and are available from several sources including the Klarity VersaFrames sold by Bionix Radiation Therapy, Toledo, Ohio. The individual mask is sent for custom fitting to a manufacturer of the facial support device.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

The invention claimed is:

1. A facial support apparatus comprising a pair of cheek supports and a pair of ear connection members, wherein each cheek support extends from one of the pair of ear connection members and is adapted to cross at least a portion of each cheek of a user and wherein the cheek supports each comprise a silicone gel pad encased in an elastomeric casing and wherein the silicone gel pad has a fixed three dimensional shape that is adapted and dimensioned to apply downward pressure to a facial structure underlying placement of the silicone gel pad when the apparatus is applied to a subject.

2. The facial support apparatus of claim 1 wherein each cheek support comprises a support armature.

3. The facial support apparatus of claim 2, wherein the support armature is a moldable structure enabling form fitting to a user's facial anatomy.

4. The facial support apparatus of claim 3, wherein the moldable structure comprises a thermoplastic or a moldable metal or combinations thereof.

5. The facial support apparatus of claim 2, wherein the support armature is inserted in a sleeve formed in the elastomeric casing.

6. The facial support apparatus of claim 1, wherein at least a portion of an inner skin facing surface of the elastomeric casing is adapted to be releasably self-adhesive to a user's skin.

7. The facial support apparatus of claim 6, wherein the elastomeric casing comprises an inner skin facing adhesive layer and an outer non-adhesive layer wherein the inner and outer layers form the elastomeric casing that encloses the silicone gel pad.

8. The facial support apparatus of claim 6, wherein at least a portion of an inner skin facing surface of the elastomeric casing is medical grade silicone sheeting.

9. The facial support apparatus of claim 1, wherein the cheek supports are releasably connected to the ear connection members.

10. The facial support apparatus of claim 9, wherein the cheek supports are releasably connected to the ear connection members by a hook and loop mechanism.

11. The facial support apparatus of claim 9, wherein the cheek supports are releasably connected to the ear connection members by a locking slot and catch-up pin mechanism.

12. The facial support apparatus of claim 1, further comprising a chin support that is connected to and extends between the pair of ear connection members.

13. The facial support apparatus of claim 1, further comprising a pair of mandible supports wherein each mandible support extends from one of the pair of ear connection members.

14. The facial support apparatus of claim 1, further comprising a forehead support attaching to and extending between each of the ear connection members.

15. The facial support apparatus of claim 1, further comprising a back neck strap connected with the ear connection members.

16. The facial support apparatus of claim 1, wherein the ear connection member includes an ear bud.

17. A facial support apparatus comprising:
a pair of facial structure supports each including an internal semi-rigid support armature and an internal non-flowable silicone gel pad having a fixed three dimensional shape that is adapted to apply support and shaping pressure to underlying facial structures when applied to a face of a subject, both encased in an elastomeric casing;
a pair of ear connection members each of which are attached to each of the pair of facial structure supports; and
a forehead support attached to and connecting the pair of ear connection members.

18. The facial support apparatus of claim 17, wherein the pair of facial structure supports are connected by a connecting member configured to cross a ventral aspect of a person's face.

19. The facial support apparatus of claim 18, wherein the connecting member configured to cross a ventral aspect of a person's face is releasably and adjustably fastened to the facial structure supports.

20. The facial support apparatus of claim 19, wherein connecting member configured to cross a ventral aspect of a person's face is releasably and adjustably fastened to the facial structure supports by a hook and loop mechanism.

21. The facial support apparatus of claim 17, wherein the pair of facial structure supports are cheek supports.

22. The facial support apparatus of claim 17, wherein the pair of facial structure supports are mandible supports.

23. The facial support apparatus of claim 17, comprising a plurality of facial structure supports including a pair of cheek supports and a pair of mandible supports.

* * * * *